United States Patent [19]

Ohsuga et al.

[11] Patent Number: 5,357,749
[45] Date of Patent: Oct. 25, 1994

[54] APPARATUS FOR CONTROLLING EXHAUST CONCENTRATION

[75] Inventors: Minoru Ohsuga, Katsuta; Toshimichi Minowa, Ibaraki; Nobuo Kurihara, Hitachiota; Yoshishige Ohyama, Katsuta, all of Japan

[73] Assignee: Hitachi Ltd., Tokyo, Japan

[21] Appl. No.: 883,200

[22] Filed: May 14, 1992

[30] Foreign Application Priority Data

May 14, 1991 [JP] Japan .................. 3-107951

[51] Int. Cl.$^5$ ............................................. F01N 3/20
[52] U.S. Cl. ..................... 60/274; 60/276; 60/298; 60/300; 60/301; 60/286; 60/289
[58] Field of Search ............... 60/274, 276, 301, 298, 60/300, 289, 286

[56] References Cited

U.S. PATENT DOCUMENTS

| | | | |
|---|---|---|---|
| 3,820,327 | 6/1974 | Henault | 60/298 |
| 3,910,042 | 10/1975 | Yuge | 60/298 |
| 4,297,328 | 10/1981 | Ritscher | 60/301 |
| 4,870,938 | 10/1989 | Nakaniwa | 60/276 |
| 4,964,271 | 10/1990 | Sawada et al. | |
| 5,083,427 | 1/1992 | Anderson | 60/274 |

FOREIGN PATENT DOCUMENTS

| | | |
|---|---|---|
| 0310120A2 | 4/1989 | European Pat. Off. |
| 2621609 | 12/1976 | Fed. Rep. of Germany |
| 2216705B2 | 9/1977 | Fed. Rep. of Germany |

OTHER PUBLICATIONS

"Catalytic $NO_x$ Reduction in Net Oxidizing Exhaust Gas", W. Held et al, SAE-Papers 1990, Paper No. 900496.
SAE Technical Paper Series, 920091. Feb. 1992.
Japanese Patent Unexamined Publication No. 2-91443 Mar. 1990.
Japanese Patent Unexamined Publication No. 58-59331 Apr. 1983.
Japanese Patent Unexamined Publication No. 1-203609 Aug. 1989.
Japanese Patent Unexamined Publication No. 1-262311 Oct. 1989.
Japanese Patent Unexamined Publication No. 3-74514 Mar. 1991.
Japanese Patent Unexamined Publication No. 3-124909 May 1991.
Japanese Patent Unexamined Publication No. 3-156142 Jul. 1991.

Primary Examiner—Douglas Hart
Attorney, Agent, or Firm—Antonelli, Terry, Stout & Kraus

[57] ABSTRACT

A NOx reducing catalyst can most efficiently remove both NOx and HC when concentrations of NOx and HC in exhaust have a specified relationship between them. For this purpose, an apparatus is adapted to control the concentrations of NOx and HC at an upstream of a catalyst to have a specified relationship. Sensors for detecting the concentration of NOx and HC are arranged at an upstream side of the catalyst. Additionally, a device for levelling a quantity of HC discharge is disposed to suppress variation thereof.

25 Claims, 25 Drawing Sheets

LEAN AIR FUEL RATIO

F I G. 15A
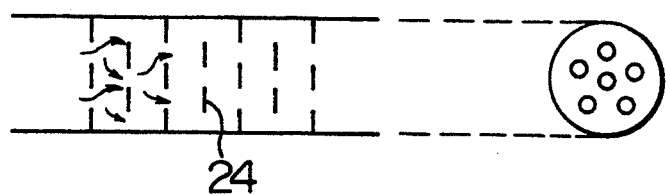
F I G. 15B
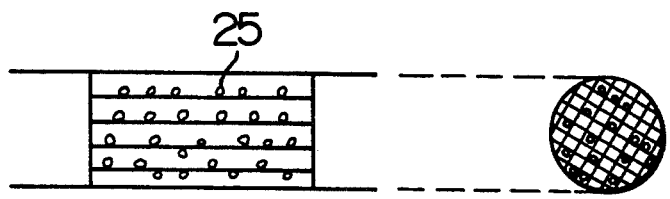
F I G. 16
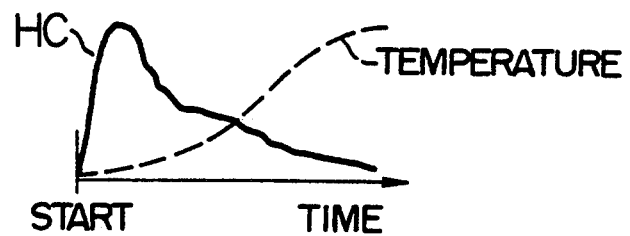
F I G. 17
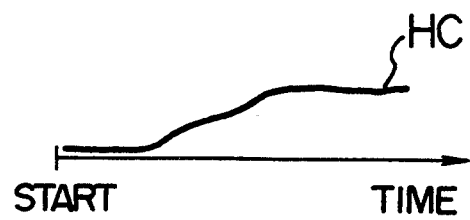

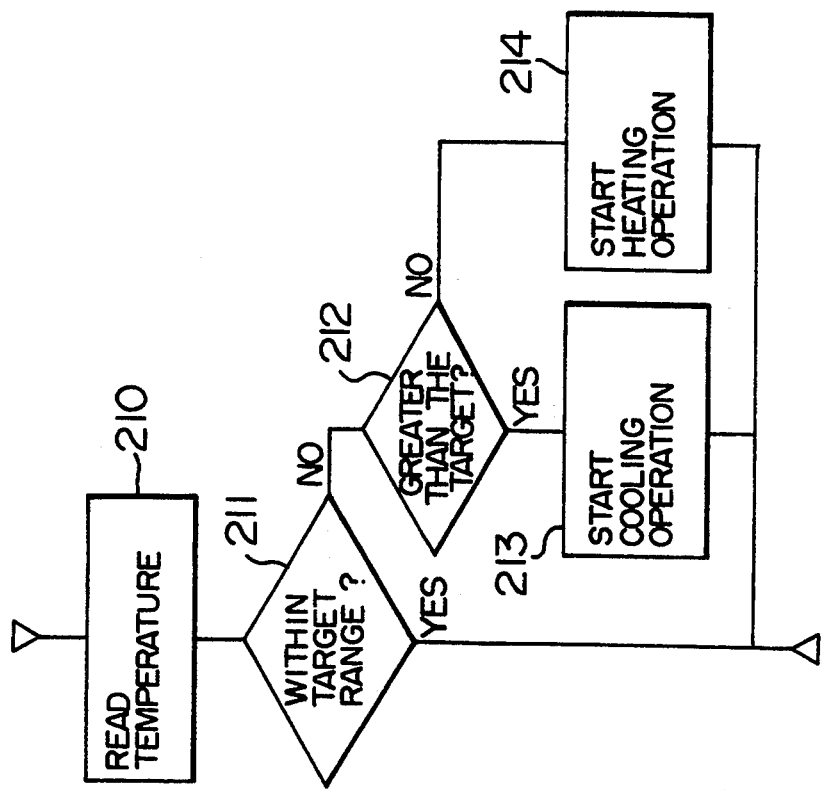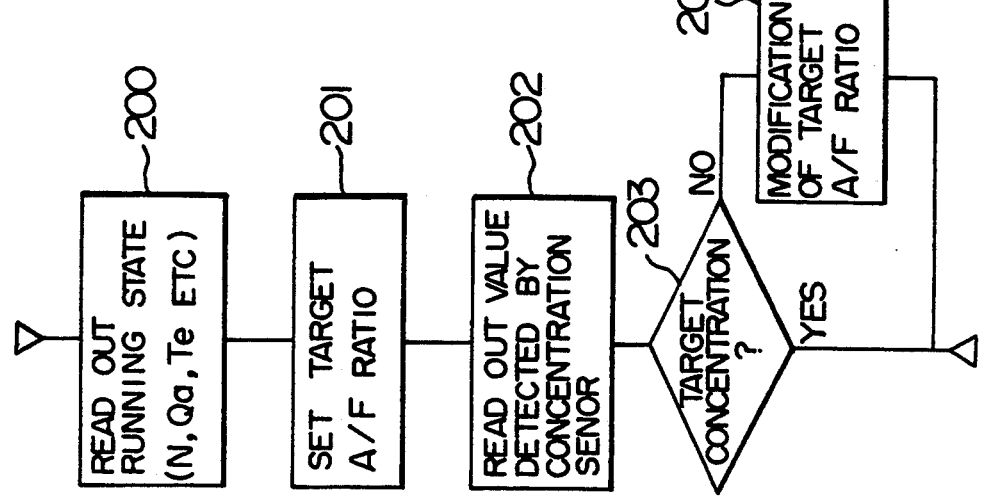

F I G. 34
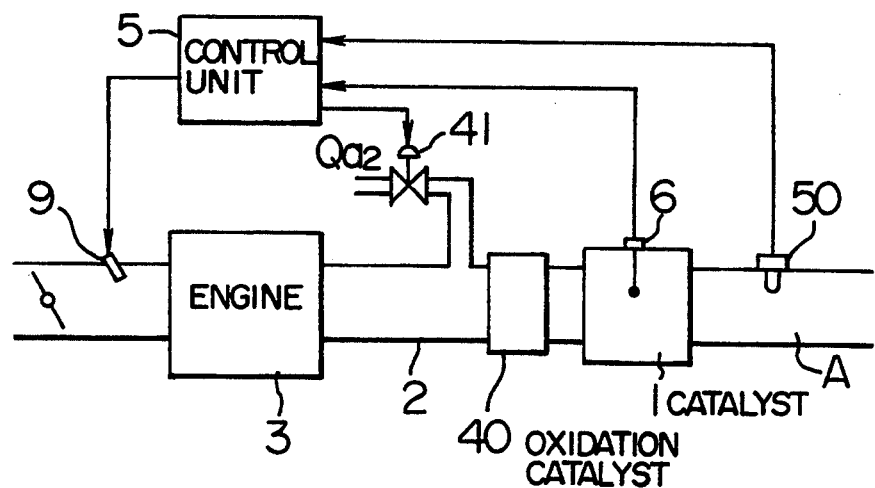
F I G. 35
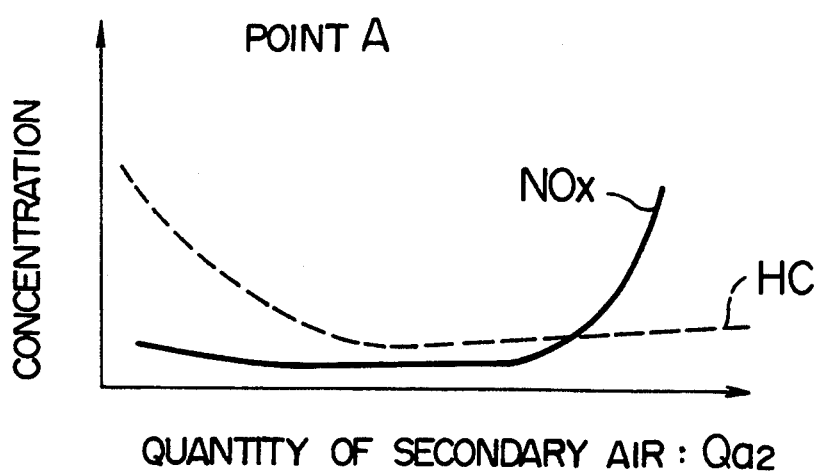

F I G. 45
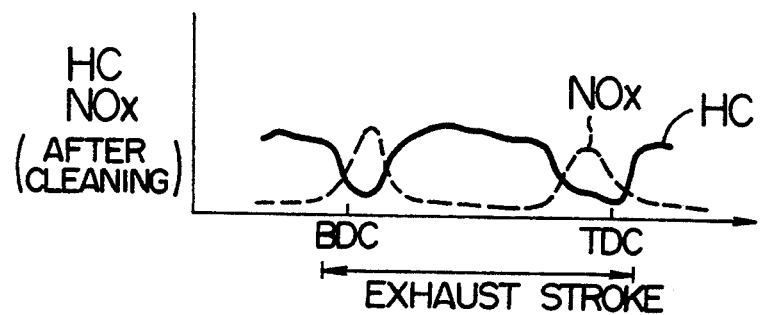
F I G. 46
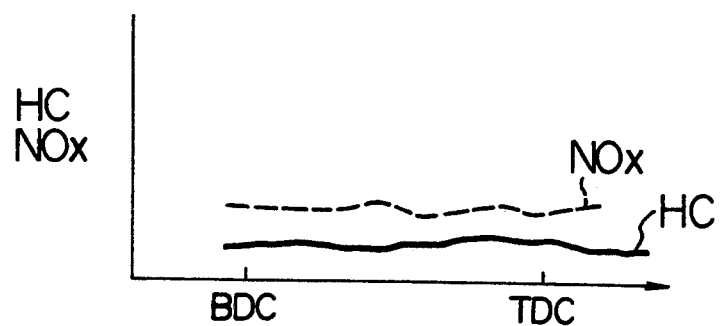
F I G. 47
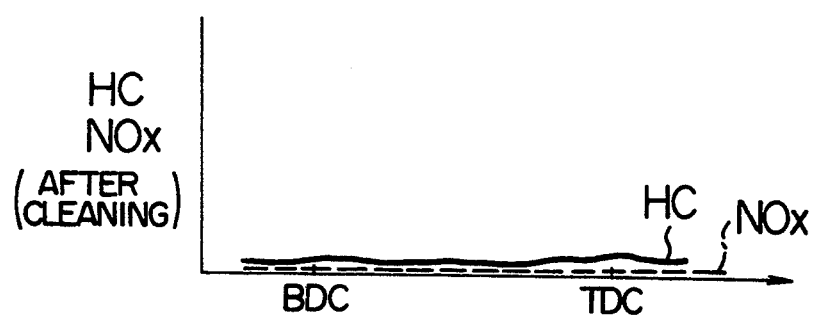

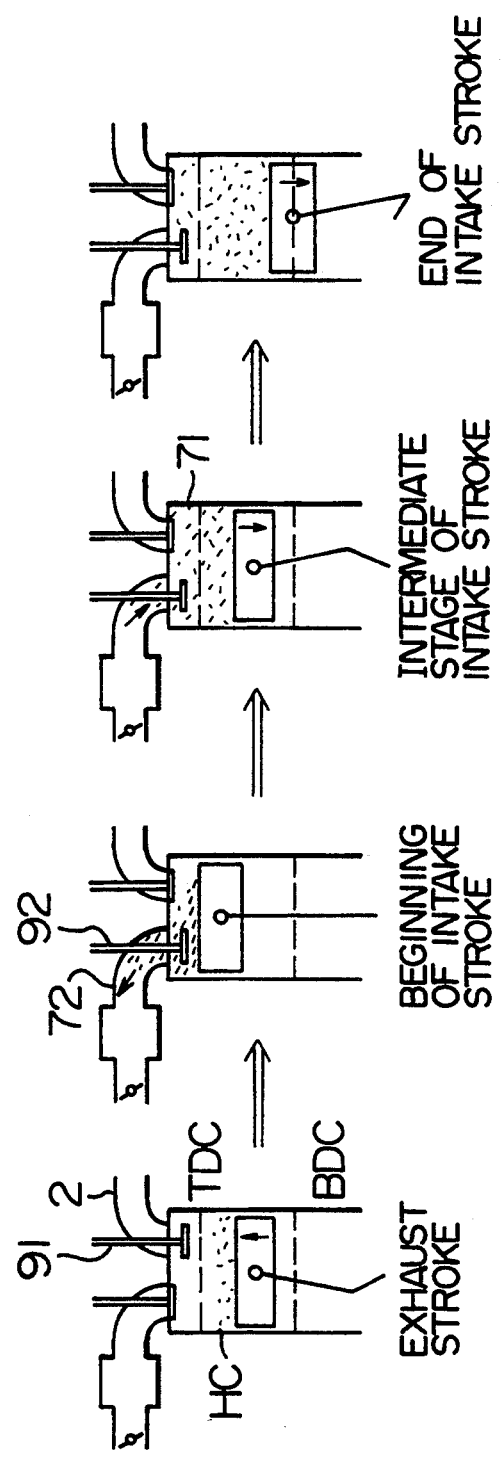

APPARATUS FOR CONTROLLING EXHAUST CONCENTRATION

BACKGROUND OF THE INVENTION

The present invention relates to an exhaust cleaning apparatus for cleaning an exhaust gas of an internal combustion engine, and more particularly relates to an apparatus and method of control of exhaust gas emission, employing a catalyst which is capable of reducing nitrogen oxides (NOx) even in an oxidizing atmosphere.

A prior art apparatus, such as that described in Japanese Patent Laid-open (Unexamined) Publication No. 58-5931, is intended to detect only hydrocarbon (HC) concentration and to control the air-fuel ratio in such a way that the HC concentration does not exceed a specified value in order to avoid a misfiring or flame-out, but is not intended to control a plurality of exhaust concentrations so as to improve reduction or cleaning efficiency of a catalyst, as performed in the apparatus according to the present invention.

In another prior art apparatus, such as that disclosed in Japanese Patent Laid-open (Unexamined) Publication No. 2-91443, a feedback to a stoichiometric air-fuel ratio and detection of carbon monoxide (CO) in a transient period are combined together. The apparatus, however, is devised to control adaptively a spike in an amount of CO in the transient period, but not to provide any means to improve reduction or cleaning efficiency of a catalyst.

SUMMARY OF THE INVENTION

An object of the present invention is to bring about a state in which a catalyst can operate at maximum efficiency, the catalyst used being capable of reducing NOx even in an oxidizing atmosphere.

In order to achieve the above-stated object, a device for controlling exhaust concentration at a predetermined or specified value (level) at the upstream side of a catalyst and a device for maintaining the temperature of the catalyst within a specified range are necessary.

When the ratio NOx/HC reaches a specified value, the catalyst removes NOx and HC simultaneously. The reduction or cleaning efficiency of the catalyst varies with a temperature and reaches the highest value within a specified range of temperature.

Since the apparatus according to the present invention can efficiently remove NOx regardless of the operating condition of an internal combustion engine, it can simultaneously meet the requirements, both for exhaust cleaning and fuel consumption, at high levels.

BRIEF DESCRIPTION OF THE DRAWINGS

FIGS. 15A and B are simplified views of another HC discharge levelling device;

FIG. 16 is a graph showing HC discharge characteristic;

FIG. 17 is a graph showing a characteristic of discharging HC;

FIG. 20 is a flowchart showing a controlling process;

FIG. 21 is a flowchart showing a controlling process;

FIG. 34 is a diagrammatic illustration of a still another embodiment of the invention;

FIG. 35 is a graph showing NOx and HC concentration characteristics;

FIG. 45 is a graph showing HC cleaning characteristic;

FIG. 46 is a graph showing an exhaust discharge rate;

FIG. 47 is a graph showing NOx and HC removing characteristics;

FIG. 59 is a view showing exhaust stroke and intake stroke;

DESCRIPTION OF THE PREFERRED EMBODIMENT

Figure 1:
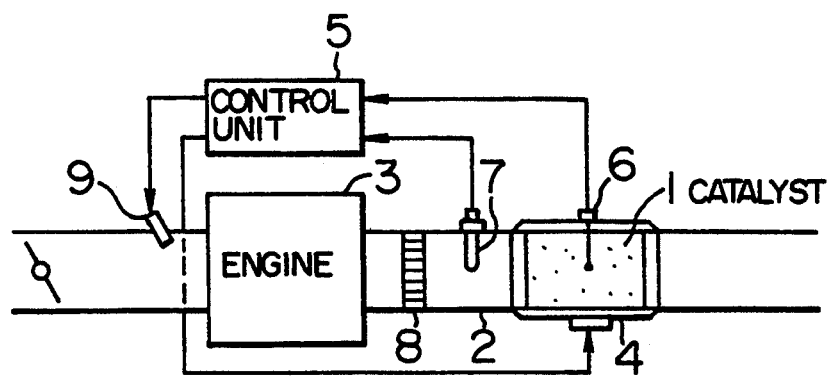
FIG. 1 is a simplified illustration of an embodiment of the invention.

FIG. 1 shows an embodiment according to the present invention. As seen in FIG. 1, a catalyst 1 for reducing Nox is mounted in the exhaust tube 2 and operates to clean the exhaust gas discharged from the engine 3. In the case of a NOx reducing catalyst or lean NOx catalyst, the range of temperatures which results in good reducing or cleaning efficiency is limited. The embodiment is equipped with a heating/cooling system 4 to control the temperature to be within an appropriate range, and the system 4 operates according to a signal from a control unit 5. The system 4 drives a heating unit to warm up the catalyst and control it at a temperature corresponding to that required for good reduction efficiency when the engine 3 is cold, while the system drives a cooling unit to cool the catalyst 1 to a temperature producing good reduction efficiency after the engine 3 has been warmed. Thus, controlling the temperature of the catalyst 1 allows the catalyst 1 to be always kept in the state of operation for good efficiency. To achieve this control of temperature, the temperature of the catalyst 1 is detected by means of a temperature sensor 6 and the temperature signal is input to the control unit 5.

The NOx reducing catalyst or lean Nox catalyst 1 may best decrease both NOx and HC when the concentrations of NOx and HC in an exhaust gas have a predetermined relationship. The embodiment is therefore realized in such a way that the concentrations of NOx and HC in the exhaust gas which flows at the upstream side of the catalyst 1, is controlled in a specified relationship. To obtain this relationship, the sensor 7 which detects the concentrations of NOx and HC is disposed at the upstream side of the catalyst 1.

As mentioned later, the concentrations of Nox and HC can be estimated from an air-fuel ratio and operating or driving conditions (engine speed, load, and temperature). In this case, the sensor 7 may be a sensor for detecting an air-fuel ratio.

The concentration of HC in an exhaust gas from an engine continuously varies corresponding to the operation of the exhaust valves. Thus, the concentration of HC at the upstream side of the catalyst 1 also continuously varies, and therefore an optimum relationship between NOx and HC can not be maintained. The embodiment of the present invention is equipped with a member 8 for smoothing or levelling the flow of HC to make more even the continuous variation of HC. Moreover, it is also possible to smooth or level the concentration of HC in the exhaust gas by further atomizing particles of fuel injected from the injection valves 9.

Figure 2:
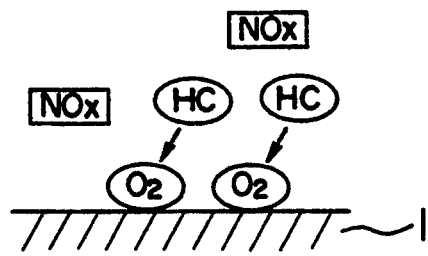
FIG. 2 is a view illustrating the principle of reduction performed by a catalyst.
Figure 3:
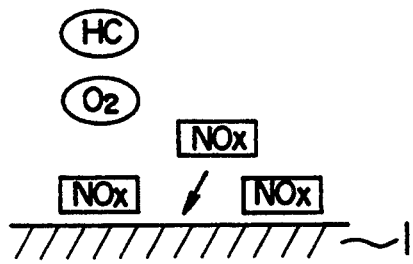
FIG. 3 is another view showing the principle of reduction performed by a catalyst.

FIGS. 2 and 3 show a principle of NOx reduction effected by a NOx reducing catalyst. This catalyst 1 can reduce NOx even in an oxidizing atmosphere in which oxygen is present. As shown in FIG. 2, first, HC explosively reacts with oxygen on a surface of the catalyst 1, and removes oxygen from the surface of the catalyst 1.

As seen in FIG. 3, next, NOx is adsorbed on the surface of the catalyst 1 selectively and is reduced. Thus, NOx and HC are simultaneously removed. In the next stage, HC again reacts with oxygen on the surface of the catalyst 1. On the principle thus explained, NOx can be removed even in an oxidizing atmosphere. As mentioned above, the present invention relates to an apparatus for efficiently controlling the operation of this catalyst and a method for controlling it.

Figure 4:
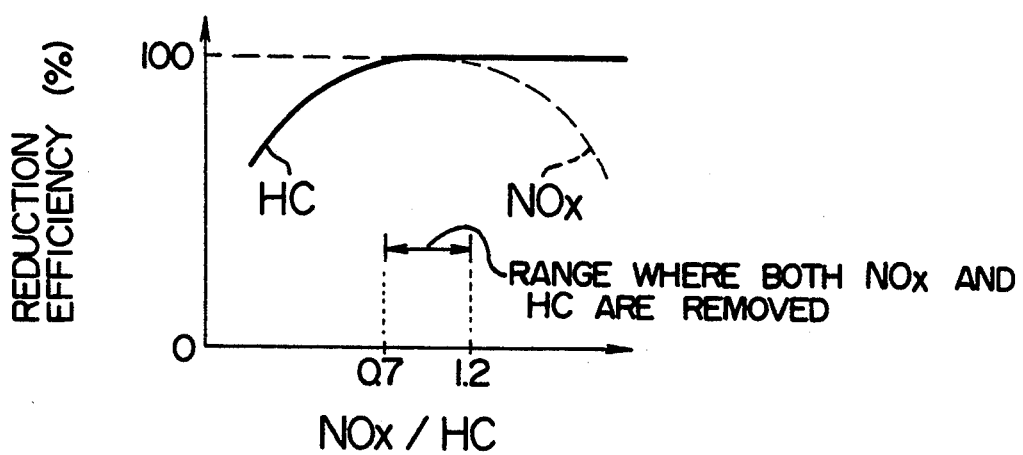
FIG. 4 is a graph showing reduction characteristic of a catalyst.

Referring to FIG. 4, a characteristic of a NOx reducing catalyst will be described. A relationship between a NOx-HC ratio, i.e. NOx/HC, and removal or cleaning efficiency is shown in FIG. 4. When the NOx-HC ratio is small or low and HC is present in large quantity, all of the NOx is reduced, while HC will remain without being oxidized. On the other hand, when the NOx-HC ratio is large or high and NOx is present in large quantity, some of the NOx will remain without being reduced. Accordingly, the NOx-HC ratio must be within a range of optimum values in order that both NOx and HC are purified or removed simultaneously. Specifically, it has been experimentally found that the best NOx-HC ratio is approximately 1.2–0.7. The apparatus according to the present invention controls those concentrations in the exhaust gas to have the best ratio.

Figure 5:
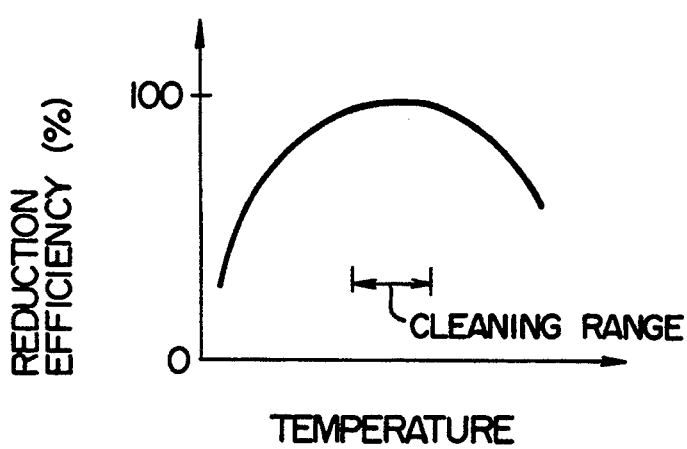
FIG. 5 is another graph showing reduction characteristic of a catalyst.

Referring to FIG. 5, a relationship between the temperature of the catalyst and the reduction efficiency of NOx is shown. When the temperature of the catalyst is either lower or higher than a certain limited range, the reduction efficiency decreases. The apparatus is equipped with a system of heating/cooling to control the temperature of the catalyst.

Figure 6:
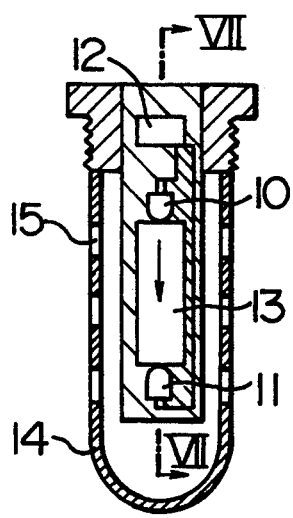
FIG. 6 is a vertical sectional view of a concentration sensor.

FIG. 6 shows an embodiment of a sensor for sensing or detecting gas concentration in an exhaust gas. This sensor measures the gas concentration on the basis of a quantity or amount of absorbed light. The sensor includes a light emitting device 10 which emits light of a specific wavelength and a light receiving device 11, and measures the gas concentration from a quantity of light which the light receiving device 11 receives when the exhaust gas passes through a passage 13. A detection circuit 12 is arranged inside the sensor. The exhaust gas is introduced through a passage 15 of a protecting tube 14 to the sensor.

Figure 7:
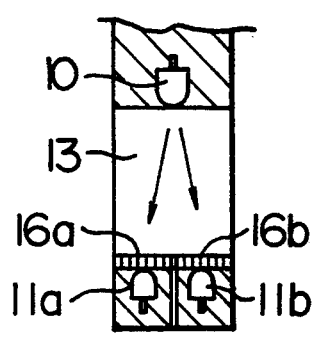
FIG. 7 is a sectional view along line VII—VII of FIG. 6.

A cross-sectional view along a line VII—VII of the sensor is illustrated in FIG. 7. In the embodiment, light from the light emitting device 10 is received by a plurality of light receiving devices 11a and 11b. In this case, optical filters 16a and 16b are disposed in front of the light receiving devices 11a and 11b to detect light of required wavelength. For example, optical filters of absorption characteristics associated with the absorption wavelength of NOx and HC are provided.

Figure 8:
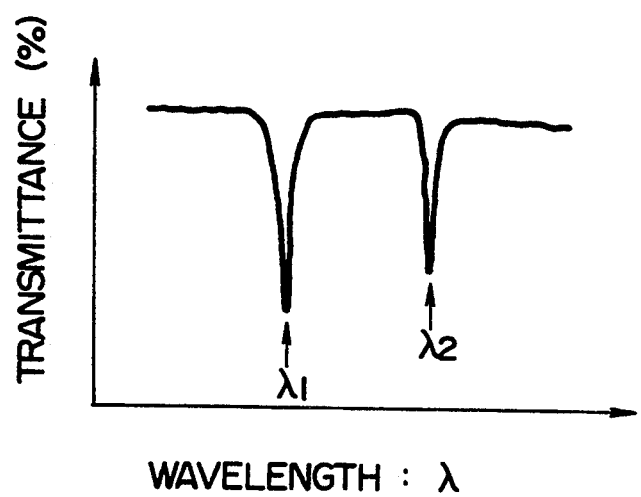
FIG. 8 is a graph showing a transmission characteristic of a filter of a sensor.

Referring to FIG. 8, a relationship between the wavelength of light and the transmittance is shown. For example, assuming that λ1 is the characteristic absorption wavelength of NOx and λ2 is the characteristic absorption wavelength of HC, light of each wavelength is absorbed by the exhaust gas and the quantity of received light of each wavelength decreases. Thus, the concentrations of the component gases are found by detecting outputs of the receiving devices.

Figure 9:
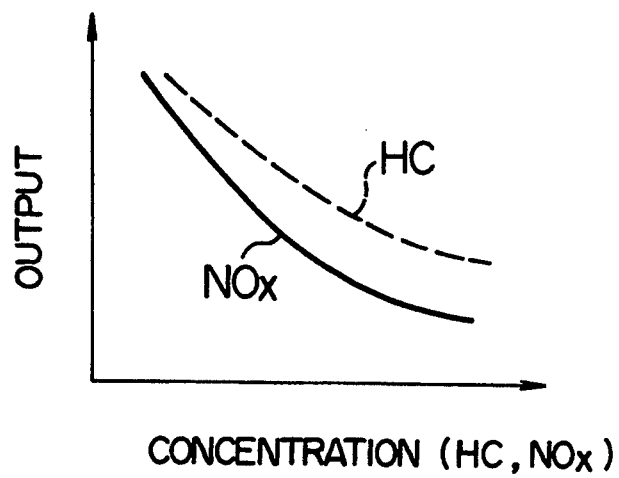
FIG. 9 is a graph showing a characteristic of a concentration sensor.

With reference to FIG. 9, a characteristic of this sensor is shown. This graph illustrates a relationship between the quantities of NOx and HC and the detection output. The detection output lowers with decreasing quantities of NOx and HC.

Figure 10:
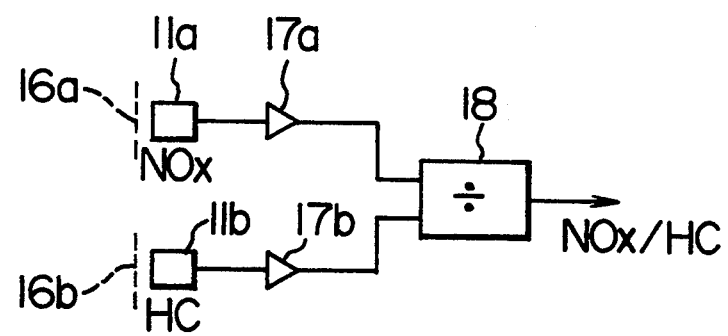
FIG. 10 is a block diagram of a unit for processing NOx-HC (Hydrocarbon) ratio.

In the case of the embodiment of the present invention, it is necessary to obtain a NOx-HC ratio in a predetermined range, and an embodiment of a circuit for delivering a value corresponding to the ratio by dividing one of the detected values by another of the detected values is shown in FIG. 10. Signals corresponding to NOx and HC from light receiving devices 11a and 11b associated respectively with the light filters 16a and 16b are amplified by amplifiers 17a and 17b. These signals are delivered to an arithmetic divider 18 and processed to be transmitted as a signal of NOx-HC ratio. This signal is delivered to the microcomputer 5.

Figure 11:
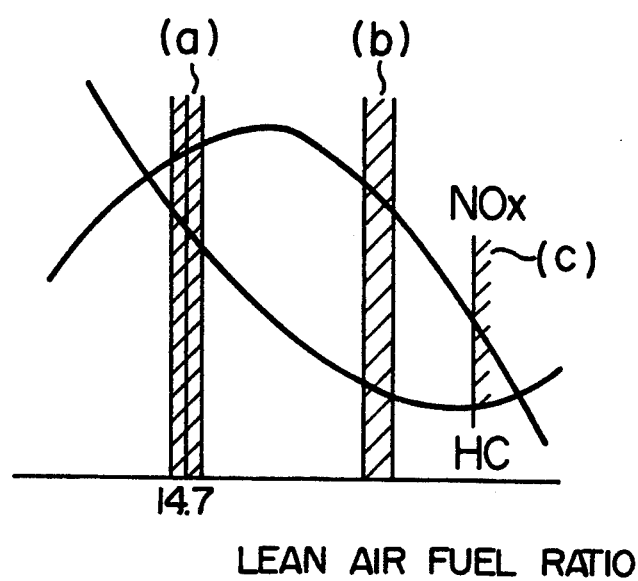
FIG. 11 is a graph showing a control air-fuel ratio.

Referring to FIG. 11, a relationship between the air-fuel ratio (air-to-fuel ratio) and the exhaust concentration will be described. In conventional apparatuses, a ternary catalyst was employed, and therefore a stoichiometric air-fuel ratio (A/F=14.7) (a) was set as a target air-fuel ratio. In the apparatus according to the present invention, the catalyst can directly reduce NOx even in a lean air-fuel ratio, and thereby the lean air-fuel ratio may be set as a target air-fuel ratio. In this embodiment of the invention, the apparatus can control to an air-fuel ratio (b), in the range of lean air-fuel ratio, in which the Nox-HC ratio becomes a value which makes it possible to provide a high reduction efficiency. The target air-fuel ratio is set to an air-fuel ratio smaller than a lean combustion limit (c). When there are a plurality of air-fuel ratios in which a NOx-HC ratio provides a high reduction efficiency, the air-fuel ratio is selectively controlled to the largest or highest one among them.

Figure 12:
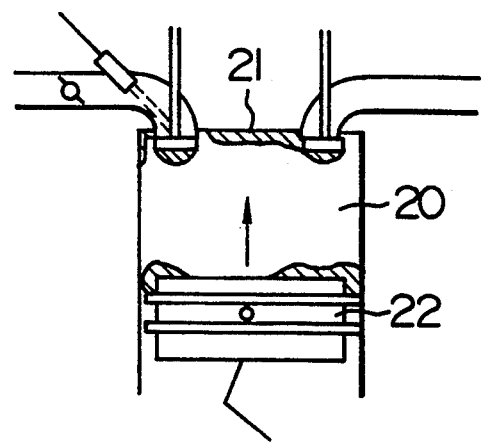
FIG. 12 is a diagram showing a principle of discharge of HC.

FIG. 12 shows the principle of discharging HC from an engine and its state of discharging. As shown in FIG. 12, liquid films of fuel, as indicated by oblique lines, are deposited on the cylinder head 21 and the head of the piston 22 in a combustion chamber 20 of the engine. This liquid film is discharged into the exhaust tube without being burnt.

Figure 13:
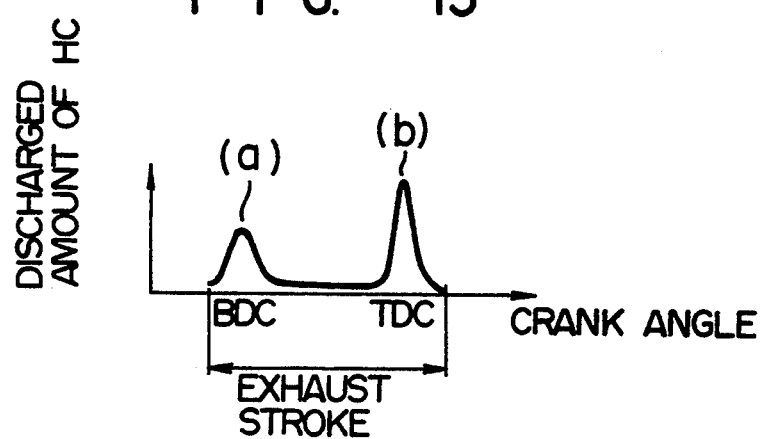
FIG. 13 is a graph showing HC discharge characteristic.

As shown in FIG. 13, in this discharge state, a large quantity of fuel deposited on the cylinder head 21, as indicated by a symbol (a), is discharged at the beginning of the exhaust stroke while fuel deposited on the head of the piston 22, as indicated by a symbol (b), is discharged at the end of the exhaust stroke. The amount of discharged HC thus will vary during the exhaust stroke. Accordingly, when a HC concentration at an upstream side of the catalyst varies, a value of the NOx-HC ratio considerably varies and the cleaning efficiency of the catalyst lowers. It is necessary to level this variation of HC.

Figure 14:
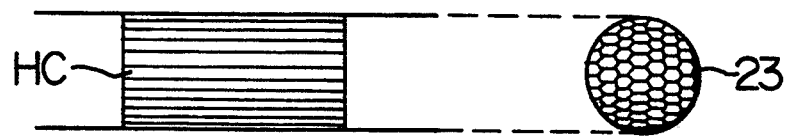
FIG. 14 is a simplified view of a HC discharge levelling device.

FIG. 14 shows a means for levelling the variation of a quantity of HC discharge. The variation of the quantity of HC discharge can be limited by this means at the upstream side of a catalyst. In FIG. 14, a honeycomb-shaped passage 23 is arranged in an exhaust tube to deposit HC therein and thereby the quantity of HC discharge is levelled.

FIG. 15A shows another embodiment in which a labyrinth type or zig-zag passage 24 for diverting a pass of exhaust gas is mounted in an exhaust tube in which HC strikes against the diverting members and the quantity of HC discharge is levelled.

FIG. 15B shows a further embodiment in which an adsorbent material 25, such as a copper ion-exchange zeolite or the like, for adsorbing HC is placed in an exhaust tube. This material adsorbs HC at a lower temperature where a large quantity of HC is discharged, while it gradually desorbs or releases HC at higher temperature where a smaller quantity of HC is discharged. Thus, the quantity of HC discharge may be levelled.

FIG. 16 shows the HC discharge immediately after the engine has started. Immediately after starting, the temperature of the exhaust is low and the quantity of HC exhaust is large. At that time, since the quantity of NOx exhaust or discharge is small, the NOx-HC ratio does not reach an optimum value, and the reduction efficiency of a NOx reducing catalyst decreases. Accordingly, the quantity of HC exhaust discharge immediately after starting must be levelled.

FIG. 17 shows an effect achieved by using an adsorbent. Since HC is adsorbed immediately after the starting of the engine, a smaller quantity of HC is drawn off into the exhaust tube. The NOx-HC ratio thus can be kept within an optimum range. As mentioned above the adsorbent is effective in levelling the amount of HC discharge or exhaust.

Figure 18:
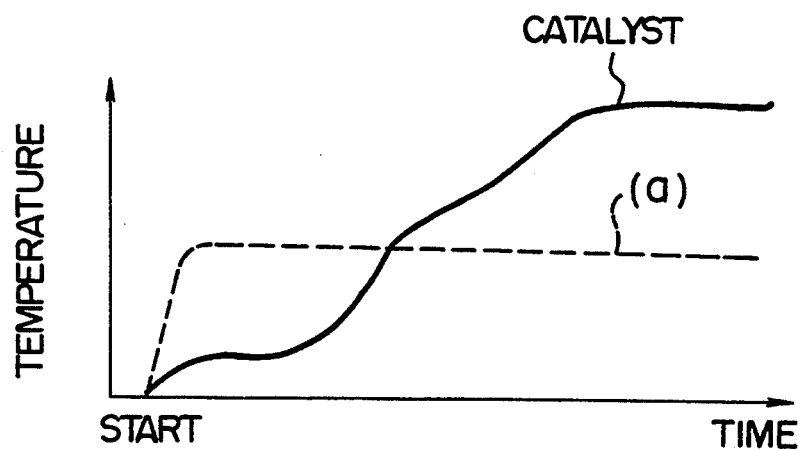
FIG. 18 is a graph showing a temperature characteristic of a catalyst.

FIG. 18 shows a method of controlling the temperature of a catalyst. FIG. 18 shows a variation of the temperature of a catalyst immediately after starting. Since the engine does not warm up yet immediately after the starting thereof, the temperature of the catalyst at that time is low, and therefore the catalyst is not yet activated and its reduction efficiency is at a low level. When an engine runs under high load, the temperature of exhaust extraordinarily rises and the reduction efficiency of the catalyst lowers again.

In order to maintain a high reduction efficiency of a NOx reducing catalyst, the temperature of the catalyst must be controlled within an optimum range. The present invention intends to always keep the catalyst in a state of high efficiency by controlling its temperature as shown by a dotted line (a).

Figure 19:
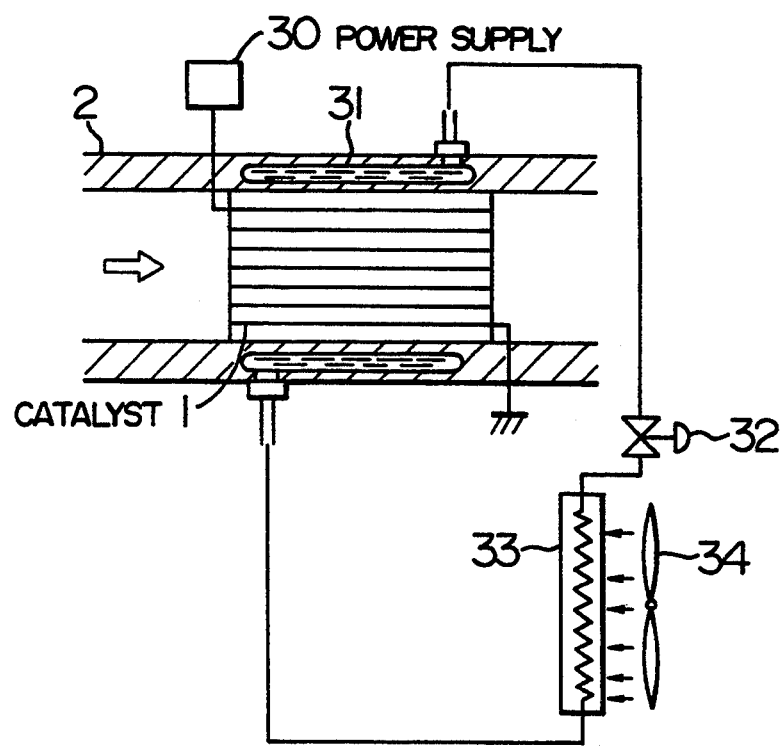
FIG. 19 is a diagrammatic illustration of a temperature controlling apparatus.

An apparatus for controlling the temperature is illustrated in FIG. 19, in which a catalyst 1 is mounted in an exhaust tube 2. This catalyst includes a metallic support or carrier which bears or carries the material of the catalyst, such as a copper ion-exchanged zeolite type catalyst.

A current is supplied from a power source 30 to this metallic support, and electrically heats the catalyst 1. At a low temperature immediately after starting, the catalyst 1 is heated up to an optimum temperature by the electrical heating. When the engine operates under high load, cooling water 31 is circulated to cool the catalyst to the optimum temperature. Control of cooling water 31 is carried out by switching on or off an electromagnetic valve 32 disposed in a cooling water piping system by a signal transmitted from a sensor 6 of the catalyst temperature. This cooling water, for example, is cooled with the radiator 33 and a fan 34. Thus, the temperature of the catalyst can be kept at the temperature of the highest reduction efficiency, by controlling the means for heating/cooling.

Referring to FIG. 20, a flowchart which illustrates a process of controlling an exhaust concentration at the upstream side of a catalyst to an optimum value, is shown. First, at a step 20, a running or operating state of the engine is read out from each sensor. The running state, for example, is represented by an engine speed N, a quantity of intake air as a load Qa, a temperature of the exhaust Te and the like. Next, at a step 201, a target air-fuel ratio A/F is set on the basis of this running state. At a step 202, when the air-fuel ratio reaches the target air-fuel ratio, a value detected at a sensor of the exhaust concentration is read Out. Next, at a step 203, this detected actual concentration is compared with the concentration which gives an optimum reduction efficiency. At a step 204, when these values do not coincide with each other, the target air-fuel ratio is modified. Thus, the concentration of exhaust gas can be always controlled to an optimum value.

FIG. 21 shows a flowchart of the operation of controlling the temperature of the catalyst. At a step 210, a value detected by a temperature sensor 6 for the catalyst is read out. At a step 211, when this actual temperature corresponds with the target value, the flow of controlling finishes. At the step 211, when the actual value is different from the target value, at a step 212, whether the actual value is larger or smaller than the target value is checked. When it is larger, at a step 213, an operation of cooling starts. When it is smaller, at a step 214, an operation of heating starts. An embodiment of an apparatus for conducting this controlling has been shown in FIG. 19.

Figure 22:
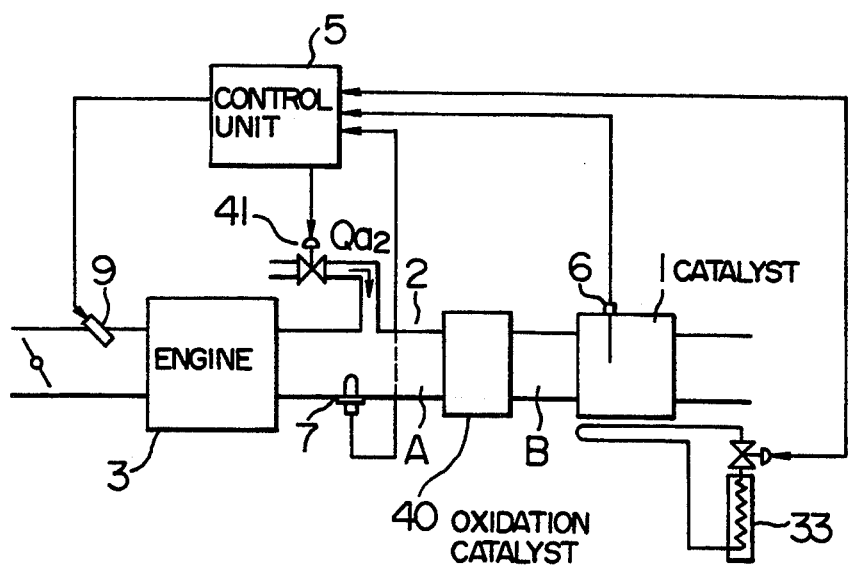
FIG. 22 is a diagrammatic illustration of another embodiment of the invention.

FIG. 22 shows another embodiment of the apparatus. In the embodiment, an oxidation catalyst 40 and a secondary air controlling valve 41 are arranged at the upstream side of a NOx reducing catalyst 1. As above mentioned, when the NOx-HC ratio has the optimum value, the reduction efficiency reaches a maximum. In this embodiment, the concentration of HC is controlled so as to have the optimum ratio value. The oxidation catalyst 40 oxidizes HC in the oxidizing atmosphere in the presence of air. The HC from the engine is oxidized through the oxidation catalyst 40 by controlling a quantity of secondary air, and thereby, the concentration of HC at the upstream side of a NOx reducing catalyst 1 is controlled to an optimum value.

Figure 23:
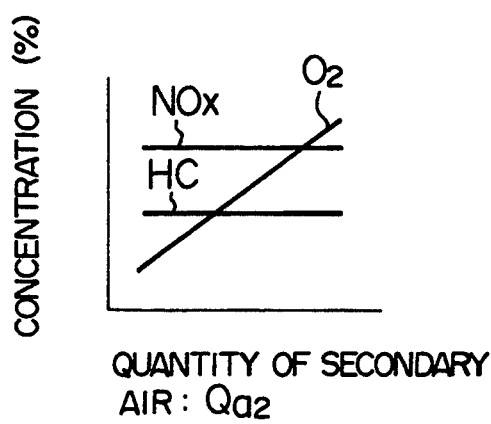
FIG. 23 is a graph showing exhaust concentration characteristic.
Figure 24:
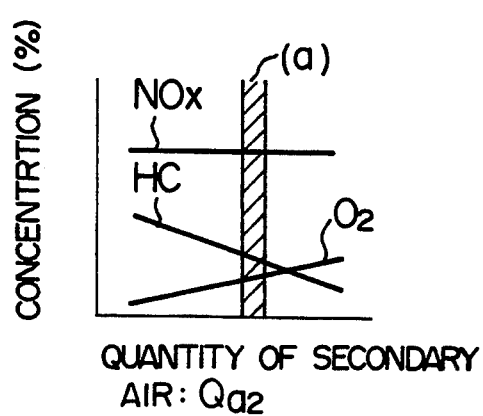
FIG. 24 is another graph showing exhaust concentration characteristic.

FIGS. 23 and 24 show the concentration of constituents or components of the exhaust gas at the upstream side A and downstream side B of the oxidation catalyst 40, respectively. In those drawings, the abscissa is representative of a quantity of secondary air Qa2 and the ordinate represents the relative concentration of component gases in the exhaust. The oxygen used for oxidation is included in the secondary air.

Even though the quantity of secondary air is increased, NOx and HC do not vary at the upstream side of the oxidation catalyst 40. With the increase in the quantity of secondary air, only the concentration of HC varies at the downstream side of the oxidation catalyst 40. Naturally, the oxygen in the secondary air also varies. Thus, the concentration of HC can be controlled by changing the quantity of secondary air.

As shown in FIG. 24, the region (a) in which the NOx-HC ratio reaches an optimum value is the target value to be achieved. The control valve 41 is controlled with a microcomputer 5 so as to obtain the quantity of secondary air corresponding to the region (a).

A decision for the control is made on the basis of a signal from the sensor 7 of gas(es) concentration in the exhaust gas. The quantity of secondary air to be introduced is decided according to a quantity of HC detected by the sensor 7, and the control valve 41 is controlled corresponding to the detected quantity. The sensor 7 may be arranged between the oxidation catalyst 40 and the NOx reducing catalyst 1. In this case, the control valve 41 is controlled while checking whether the NOx-HC ratio reaches an optimum value, i.e. this operation is effected by feedback control. The above-mentioned operation can be effective even if the engine-operating condition or the air-fuel ratio is rich or lean.

Figure 25:
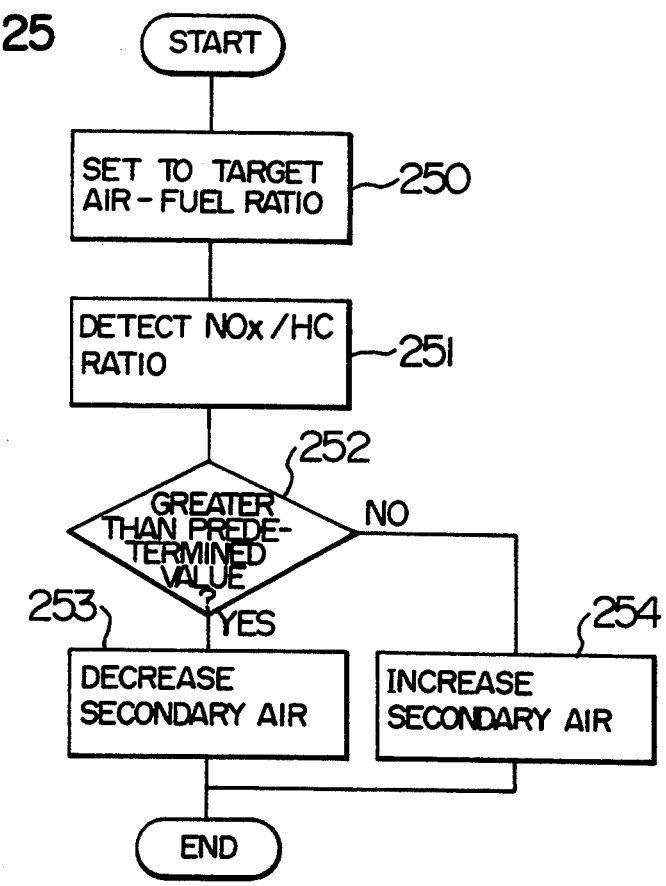
FIG. 25 is a flowchart showing a controlling process.

FIG. 25 shows a flowchart relating to another embodiment in which the sensor 7 is positioned between the oxidation catalyst 40 and the NOx reducing catalyst 1. At a step 250, control is set to a target air-fuel ratio, and at a step 251, a NOx-HC ratio is detected. When the detected value is larger than a predetermined value, the quantity of secondary air is decreased and the concentration of HC is increased at a step 253. When the detected value is smaller than the predetermined value, the quantity of secondary air is increased at a step 254. In addition, as stated later, the NOx-HC ratio may be estimated from a running or operating state, instead of the detection of the same ratio at the step 251.

Figure 26:
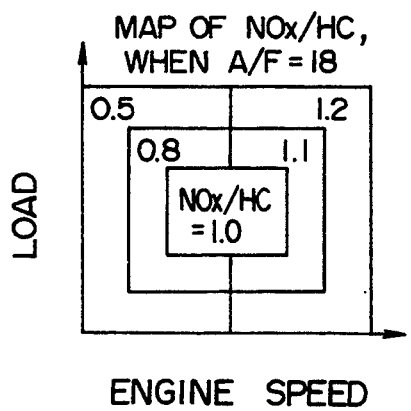
FIG. 26 is a map showing exhaust concentration.
Figure 27:
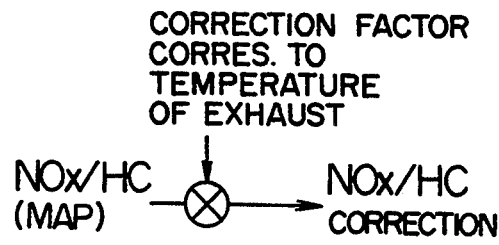
FIG. 27 is a diagram showing a method of correcting NOx-HC ratio.

FIG. 26 shows an embodiment of a method the estimating of Nox-HC ratio. As illustrated in FIG. 26, representative values of the NOx-HC ratio are stored in association with engine speed and load in the form of a map. As shown in FIG. 27, an actual concentration ratio value may be obtained by multiplying the stored ratio value by a correction factor based on the temperature of the exhaust. The correction factor is selected to be 1.0 when the exhaust temperature is 400° C. The factor is increased up to 1.5 as the temperature rises from 400° C., while the factor is decreased down to 0.5 as the temperature becomes lower from 400° C.

Figure 28:
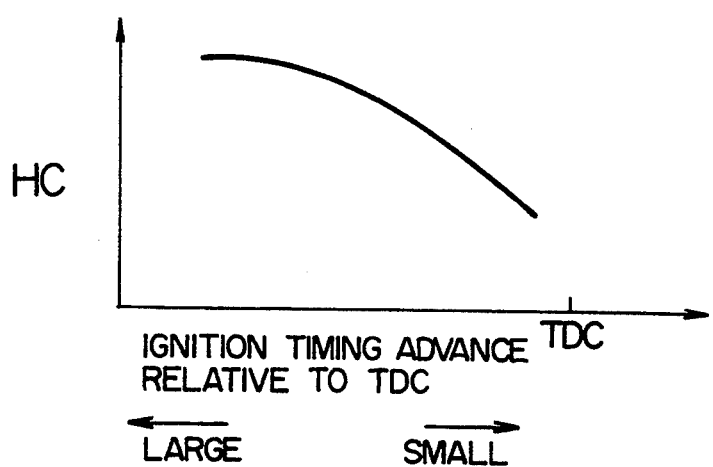
FIG. 28 is a graph showing HC discharge characteristic.

FIG. 28 shows a method of varying the quantity of HC depending on ignition or spark timing, in place of controlling the quantity of HC through an oxidation catalyst 40 shown in FIG. 22. As shown in FIG. 28, when the ignition timing decreasingly approaches TDC (Top Dead Center), a quantity of HC discharge lowers.

Figure 29:
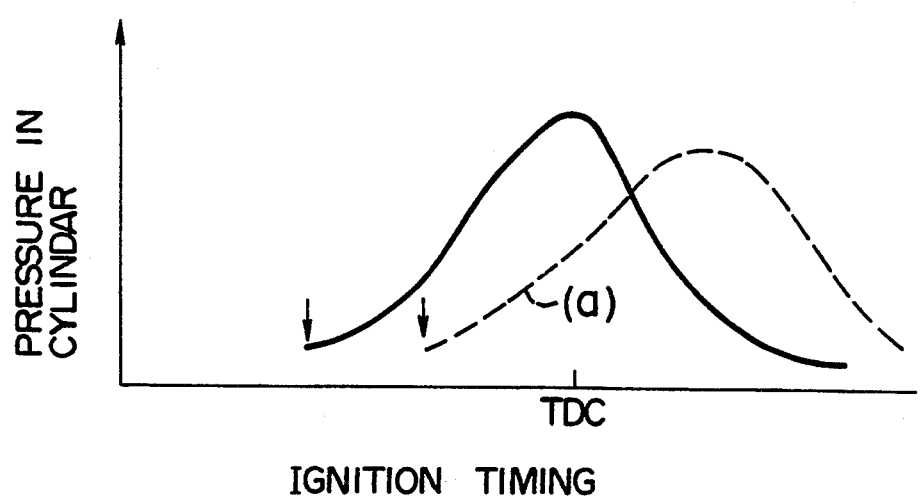
FIG. 29 is a graph showing internal pressure within cylinder characteristic.

This means that, as shown in FIG. 29, when ignition timing (arrow) is delayed as identified by (a), combustion continues even after TDC, and the HC in the combustion chamber burns, and thus the concentration of HC decreases. Thus, the concentration of HC can be controlled also by controlling ignition timing, and the NOx-HC ratio can be controlled to an optimum value.

Figure 30:
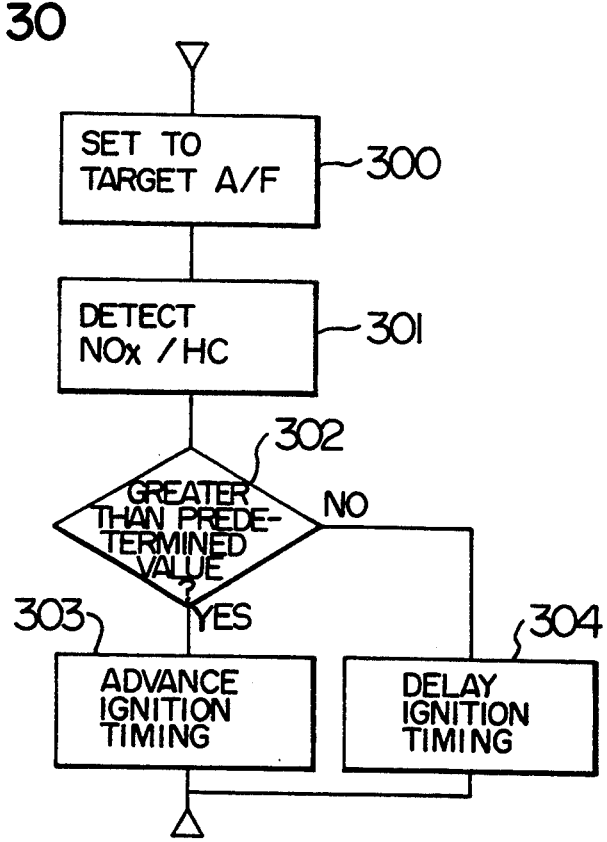
FIG. 30 is a flowchart showing a controlling process.

FIG. 30 shows a flowchart of this operation. At a step 300, the air-fuel ratio of the mixture supplied to the engine is set to a target air-fuel ratio, and at a step 301, the NOx-HC ratio is detected. At a step 302, when this value is judged to be larger than a predetermined value, at a step 303, the quantity of HC discharge is increased by advancing the ignition timing, and thereby, the NOx-HC ratio decreases. When the same value is judged to be smaller than the predetermined value, the quantity of HC discharge is decreased by delaying the ignition timing, and thereby, the NOx-HC ratio increases. The detection of the NOx-HC ratio conducted at step 301 may be achieved, following the above-mentioned procedure of estimation.

Figure 31:
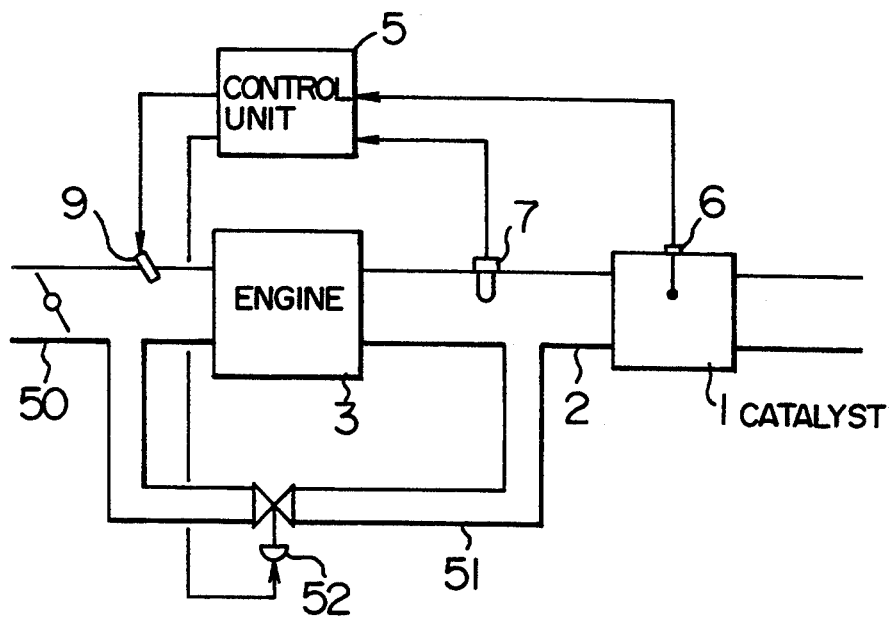
FIG. 31 is a diagrammatic illustration of still another embodiment of the invention.

Referring to FIG. 31, another method of controlling the NOx-HC ratio is shown. FIG. 31 illustrates an arrangement of an apparatus for this purpose. This apparatus controls a concentration of NOx among constituents of exhaust gas in an exhaust tube which is placed at the upstream side of a NOx reducing catalyst 1. Accordingly, a passage 51 for returning or recirculating an exhaust gas from an exhaust tube 2 to an intake tube 50, and a control valve 51 are provided. This is an exhaust recirculating apparatus.

Figure 32:
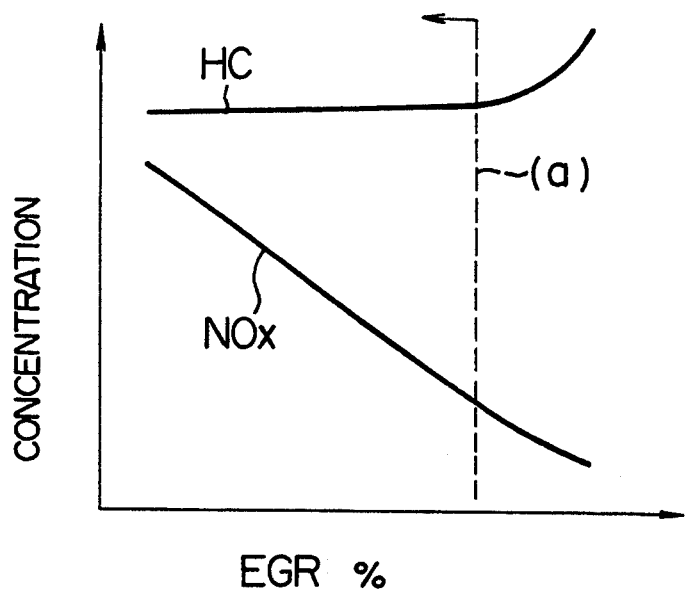
FIG. 32 is a graph showing a characteristic of EGR.

A relationship between the quantity of exhaust gas recirculation (EGR) in operation and the concentration of the exhaust is shown in FIG. 32. When the quantity of EGR increases, the quantity of NOx discharge decreases. Thus, the quantity of NOx can be controlled by varying the quantity of EGR, till a level (a) is reached where combustion turns out worse and HC begins to increase. Thus, the quantity of NOx can be controlled by operating the EGR on the basis of a value detected at a sensor 7 of concentration of NOx in the exhaust gas, in such a manner that the NOx-HC ratio reaches an optimum value.

Figure 33:
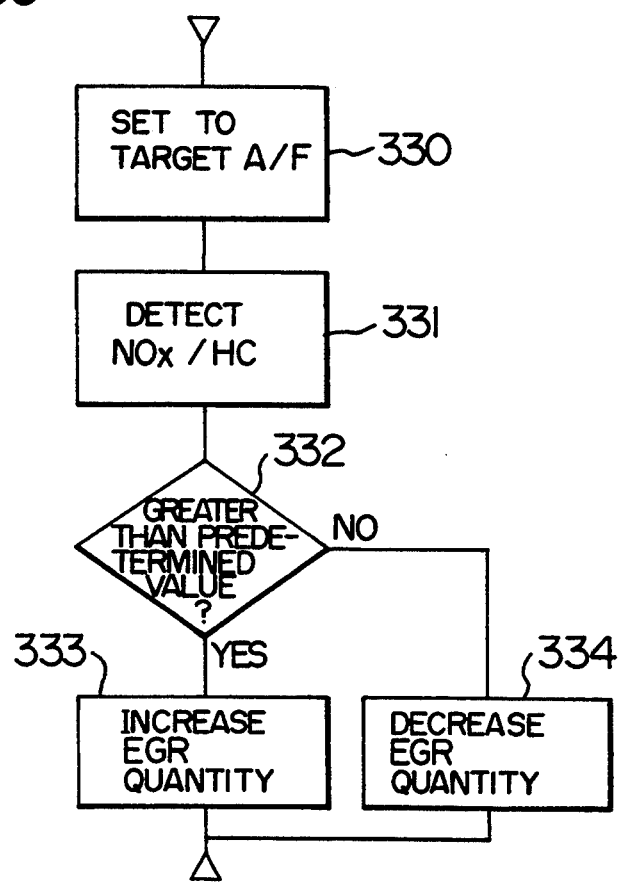
FIG. 33 is a flowchart showing a controlling process.

FIG. 33 shows a flowchart of such control. First, control is set to a target air-fuel ratio at a step 330, then the NOx-HC ratio is detected at a step 331. When the detected value is judged to be larger than a predetermined value at a step 332, the quantity of EGR is increased at a step 333. Or, when the detected value is judged to be smaller than the same value, the quantity of EGR is decreased at a step 334.

FIG. 34 shows another embodiment for controlling NOx and HC. A sensor 50 of concentration for detecting the gases in the exhaust is disposed at the downstream side of a NOx reducing catalyst 1. Concentrations of NOx and HC are controlled by controlling a control valve 41 for a quantity of secondary air on the basis of the value detected by the sensor. In this case, this control also may be achieved by the above-mentioned controlling of the ignition timing or EGR. In this embodiment, its accuracy is improved, since the quantity to be controlled is decided by detecting a result of the cleaning effect of the catalyst 1.

FIG. 35 shows a relationship, at a point A of FIG. 34, between the quantity of secondary air Qa2 and the concentration of the exhaust. When Qa2 is an optimum value, NOx and HC reach a minimum value, respectively. The quantity to be controlled is decided by a microcomputer 5 on the basis of the detected value from the sensor 50, so as to realize such optimum state.

Figure 36:
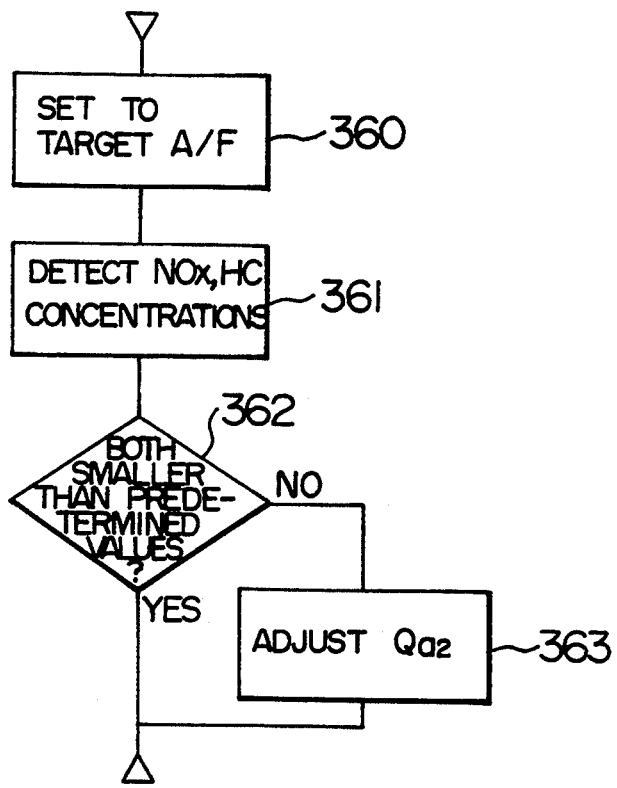
FIG. 36 is a flowchart showing a controlling process.

FIG. 36 shows a flowchart relating to the operation of this embodiment. First, control is set to a target air-fuel ratio at a step 360, and concentrations of NOx and HC are detected by a sensor 50 at a step 361. When both of them are judged to be smaller than respective predetermined values at a step 362, the flow finishes. When they are judged to be not smaller, the quantity of secondary air Qa2 is adjusted at a step 363.

Figure 37:
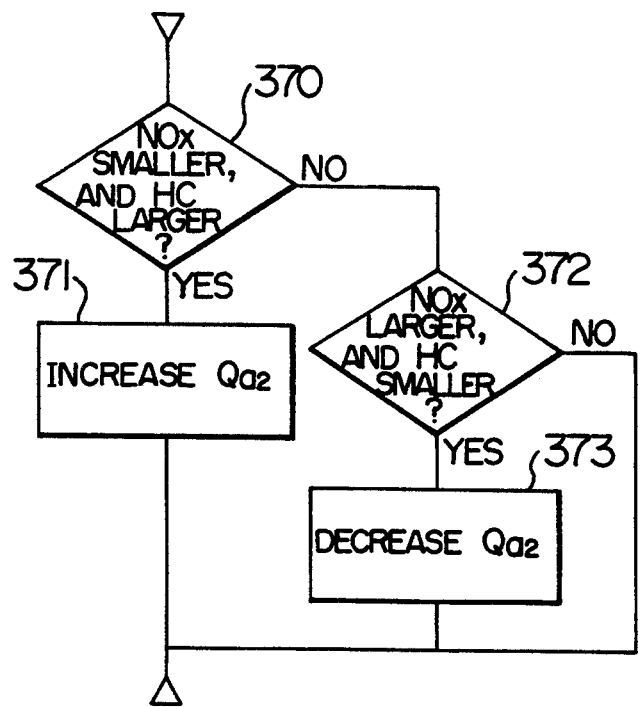
FIG. 37 is a flowchart showing a controlling process.

FIG. 37 shows a flow chart of an embodiment for adjusting the quantity of secondary air Qa2. When the concentration of NOx is smaller than its predetermined value and a concentration of HC is larger than its predetermined value at a step 370, the quantity of secondary air Qa2 is increased and only the concentration of HC is decreased at a step 371. When the concentration of NOx is larger than its predetermined value and the concentration of HC is smaller than its predetermined value at a step 372, the quantity of secondary air Qa2 is decreased and the concentration of HC is increased and thereby the NOx-HC ratio reaches an optimum value.

Figure 38:
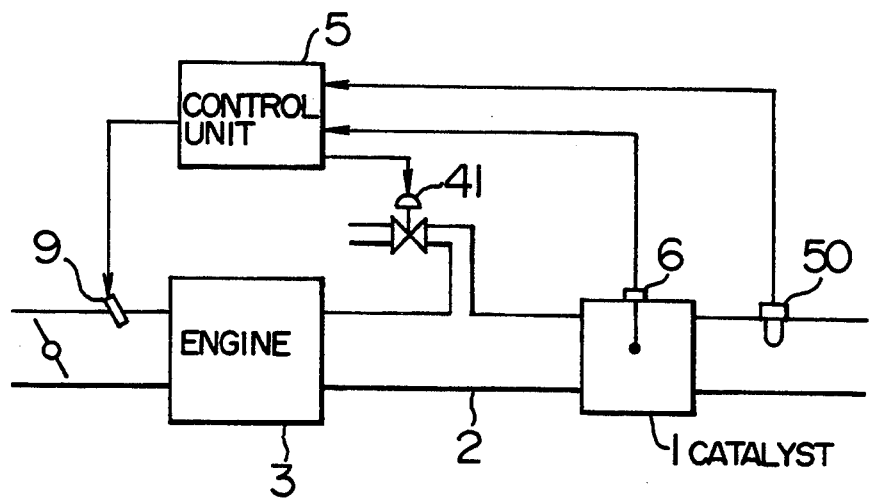
FIG. 38 is a diagrammatic illustration of still another embodiment of the invention.

FIG. 38 shows another embodiment. In this embodiment, a sensor 50 is arranged at the downstream side of a NOx reducing catalyst 1. A secondary air controlling valve 41 is controlled on the basis of a signal from the sensor 50. In this embodiment, however, an oxidation catalyst is not used. Although an effect of the embodiment is less than that utilizing the oxidation catalyst, HC can be oxidized only by introducing secondary air into an exhaust tube 2. An inventive effect can be achieved even by such a simple method. The flow of control is the same as that in FIGS. 36 and 37.

Figure 39:
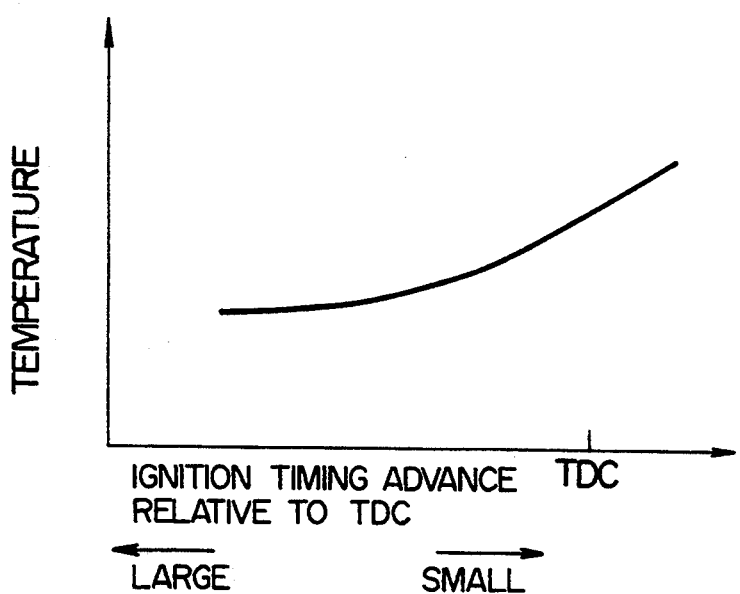
FIG. 39 is a graph showing exhaust temperature characteristic.

FIG. 39 shows another method of controlling the temperature of the catalyst 1. In this method, the temperature of the exhaust is varied by spark or ignition timing, and thereby, the temperature of the catalyst is indirectly controlled. FIG. 39 shows a relationship between the ignition timing and the temperature of the exhaust. With decreasing or delaying ignition timing, the temperature of the exhaust rises. This is because combustion continues until a later stage when ignition timing is smaller, as stated in FIGS. 28 and 29.

Figure 40:
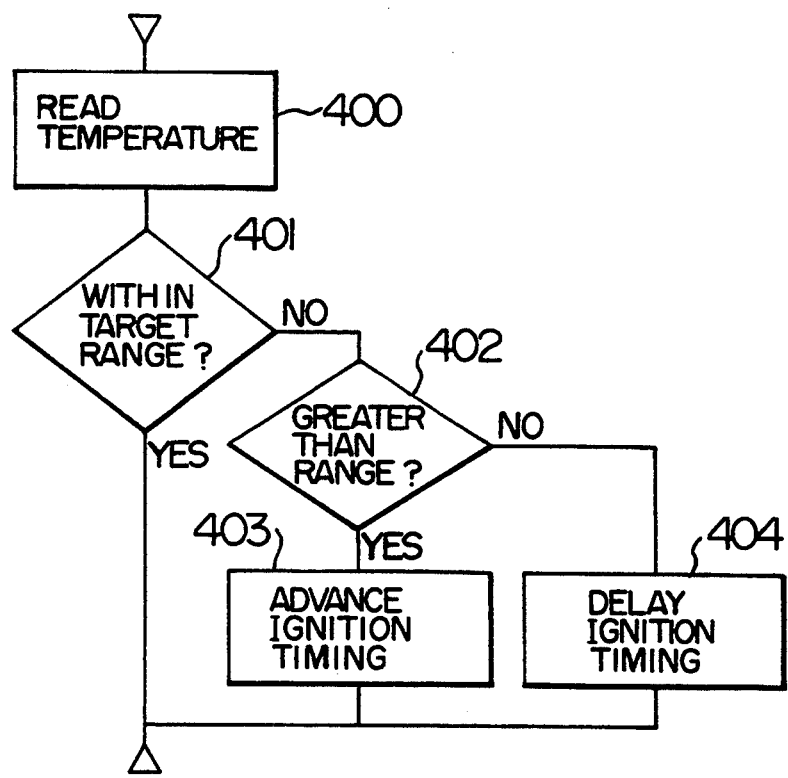
FIG. 40 is a flowchart showing a controlling process.

FIG. 40 shows a flowchart for controlling the temperature. The temperature of the catalyst is read out at a step 400, and at a step 401, when the temperature is judged to be out of a target range, and additionally, when it is judged to be larger than the target value at a step 402, ignition timing is increased (advanced) and the temperature of the exhaust is decreased, at a step 403. When the temperature of the catalyst is judged to be smaller than the target value, at a step 404, ignition timing is decreased (delayed) and the temperature of the exhaust is increased.

Figure 41:
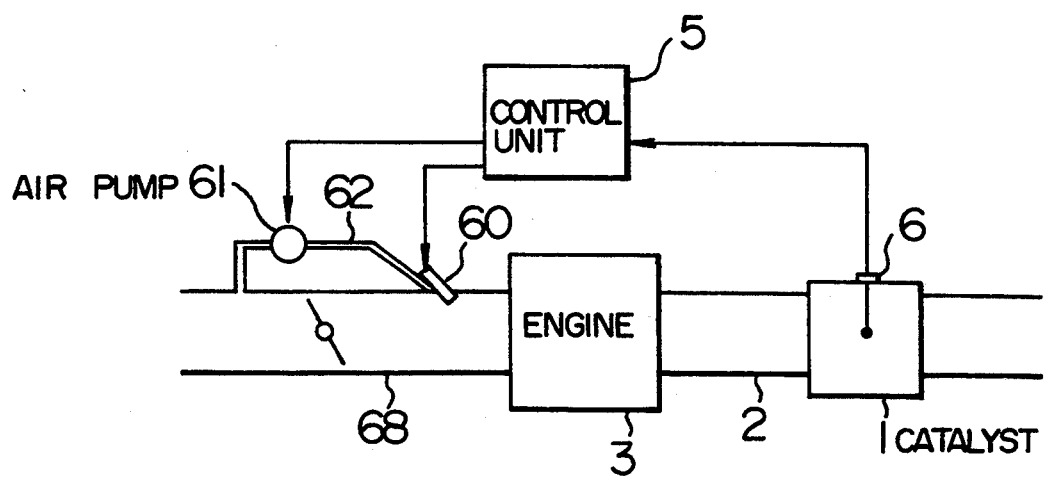
FIG. 41 is a diagrammatic illustration of still another embodiment of the invention.

FIG. 41 shows another embodiment. This embodiment is intended to level the quantity of HC discharged from the engine. Uniformization of droplets of atomized fuel supplied to the engine is effective in levelling the quantity of HC discharge. Therefore, it is necessary for an injection valve 60 to be capable of finely atomizing the fuel. In this embodiment, an injection valve for atomizing the fuel with an aid of air flow is employed. In order to supply the air for atomization, an air pump 61 is disposed which sends the air through an air passage 62 to the injection valve 60.

Figure 42:
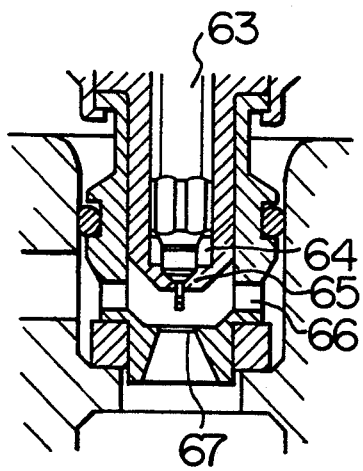
FIG. 42 is a sectional view of an injection valve.

The structure of a section of the fuel injection valve 60 is shown in FIG. 42. When a needle 63 is lifted by an electromagnet (not shown), the fuel is injected from a fuel pool 64 through an orifice 65. The air for atomization entering from an air passage 66, is directed to this injected fuel. Thereby, the fuel is atomized to fine droplets smaller than 100 $\mu$m by kinetic energy of the air. The fine droplets are injected through an injection hole 67 into an intake tube 68. The quantity of HC discharge can be levelled by means of this injection valve for producing these fine droplets of fuel.

Figure 43:
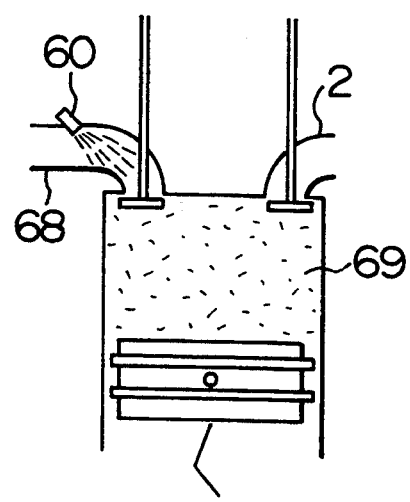
FIG. 43 is a simplified illustration showing a state of fuel in a combustion chamber in still another embodiment.

FIG. 43 shows a state of the fuel in which the fine droplets are produced according to this embodiment. In a conventional injection valve which produces relatively larger droplets, a liquid film is formed inside the intake tube 68. Therefore, the quantity of fuel entering the engine greatly varies. On the other hand, in the present embodiment which produces fine droplets, the droplets evaporate rapidly and may be easily carried with the air flow and thus do not stick inside the intake tube 68, and a liquid film is not produced. Accordingly, the liquid fuel is not produced in a combustion chamber 69 either, and the mixture of air and fuel is made more uniform. Therefore, the mixture burns uniformly, and it approaches complete combustion and the quantity of HC discharge from the engine can be levelled.

Figure 44:
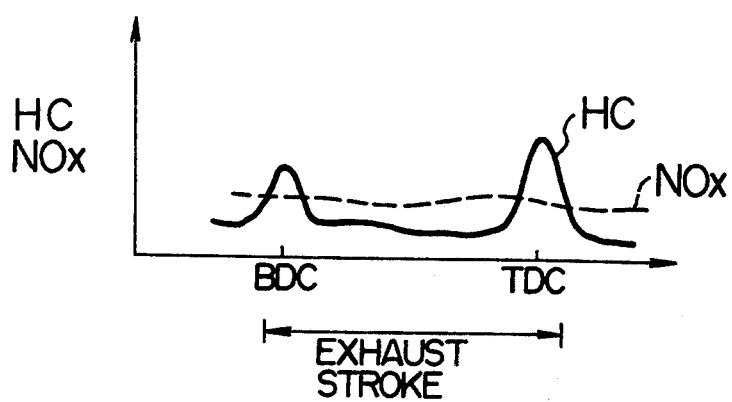
FIG. 44 is a graph showing HC discharge characteristic.

FIG. 44 shows a graph of a state of the exhaust which is produced in burning of larger droplets by a conventional apparatus. As shown in FIG. 13, HC produced in the conventional apparatus is discharged into the exhaust tube at the beginning and end of the exhaust stroke. The quantity of NOx discharge is equalized during the stroke. Therefore, the NOx-HC ratio varies depending on time and can not be kept to a value which will ensure high cleaning efficiency.

FIG. 45 shows concentrations of NOx and AC, after cleaning, downstream of the catalyst 1. Since the HC concentration varies during the exhaust stroke, both NOx and HC are reduced during the exhaust, or not reduced.

FIG. 46 is a graph showing an effect achieved by this embodiment. Since the droplets of fuel supplied to the engine are smaller, the quantity of HC discharge is equalized or levelled. Due to this equalization or levelling, the NOx-HC ratio is fixed during the exhaust stroke. Thus, the catalyst 1 is always operated under the concentration ratio of NOx to HC, in the exhaust, which gives the highest reduction efficiency.

The concentration of NOx and HC at the downstream side of the catalyst 1 is shown in FIG. 47. Both concentrations are seen to have been reduced. Using an injection valve for atomizing droplets of fuel in combination with a NOx reduction catalyst is effective.

Figure 48:
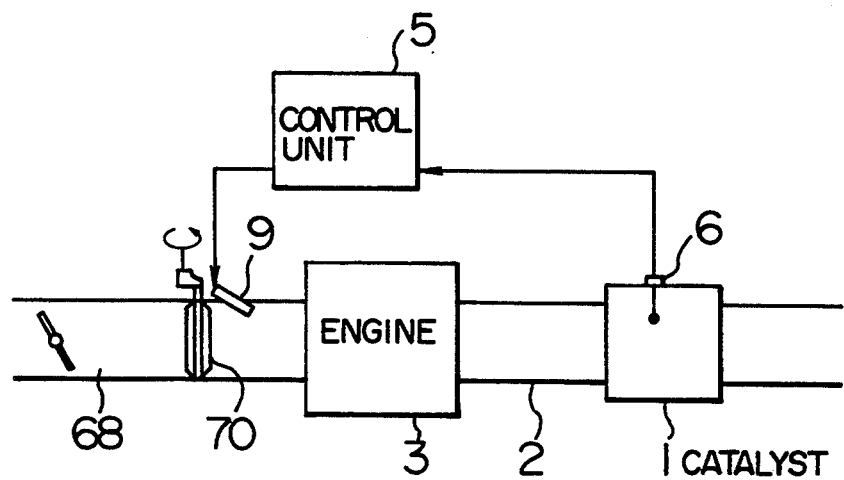
FIG. 48 is a diagrammatic illustration of still another embodiment of the invention.

FIG. 48 shows another method of levelling HC. In an intake tube 68, a swirl control valve (SCV) 70, which gives a swirl to its intake, is arranged. By means of this valve 70, swirls are produced in the combustion chamber, and the introduced fuel is mixed and uniformized. Thus, the same effect as is obtained in FIG. 41 for atomizing droplets of fuel, can be achieved. That is, the concentration of HC exhaust is levelled, the NOx-HC ratio becomes an optimum value, and the cleaning efficiency of the catalyst 1 is improved. As mentioned above, a combination of the SCV 70 with the NOx reducing catalyst is effective.

Figure 49:
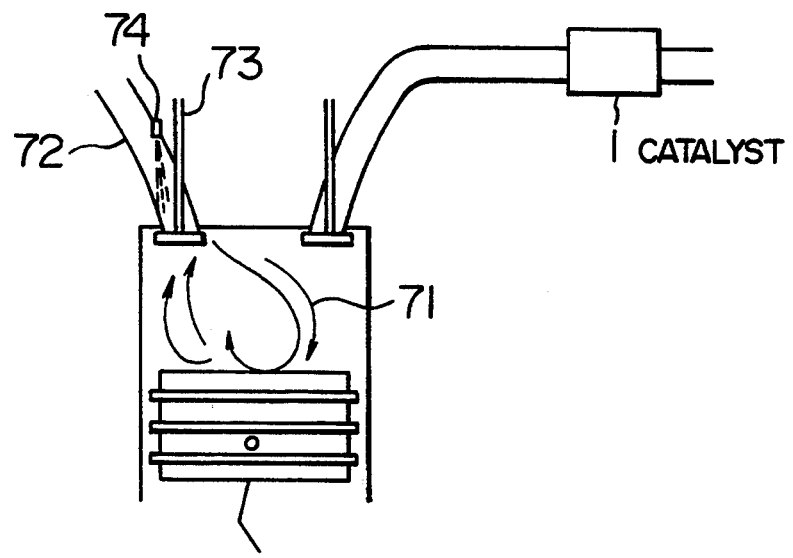
FIG. 49 is a simplified view showing flow of intake mixture.
Figure 50:
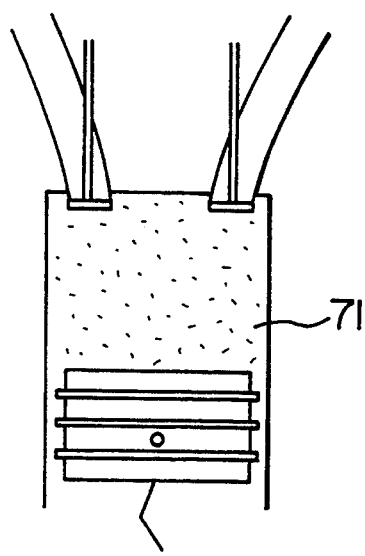
FIG. 50 is a simplified view showing a state of mixture.

FIG. 49 shows still another method of levelling HC. In the drawing, an intake tube 72 for producing longitudinal swirls 71 in a combustion chamber is provided. This intake tube 72 is such that the air-fuel mixture enters along a direction, compared with an ordinary intake tube 68, more in alignment with the direction of the intake valve stem 73. This longitudinal swirl can be maintained even during the compression stroke when the piston is moving upwards. The fuel in the combustion chamber 71 is mixed better and the mixture is uniformized. Its state is shown in FIG. 50. Since the mixture in the combustion chamber 71 is uniformized, the quantity of HC discharge is levelled and the reduction efficiency of the catalyst 1 is improved. The injection valve 74 may be an injection valve for atomizing fuel by air flow.

Figure 51:
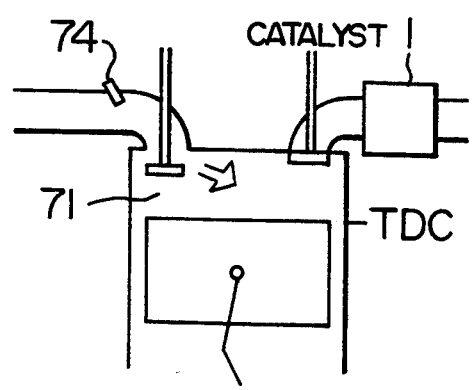
FIG. 51 is a diagrammatic illustration of a still another embodiment of the invention.
Figure 52:
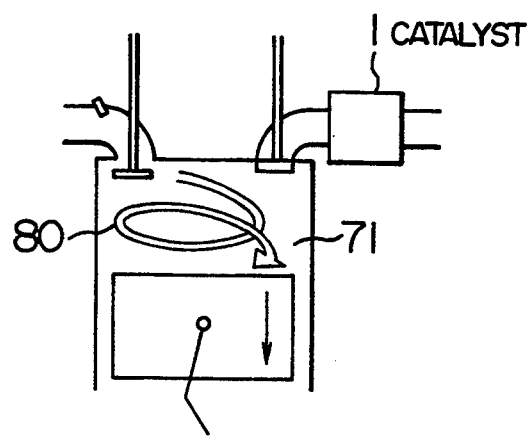
FIG. 52 is a simplified view showing flow of intake mixture.

FIG. 51 shows a still another method of levelling HC. Intake 80 which enters the combustion chamber 71 is swirling to some extent during an intake stroke as shown in FIG. 52. When the fuel is injected into the swirling flow during this intake stroke, the fuel is mixed in the combustion chamber 71 and the mixture is uniformized.

Figure 53:
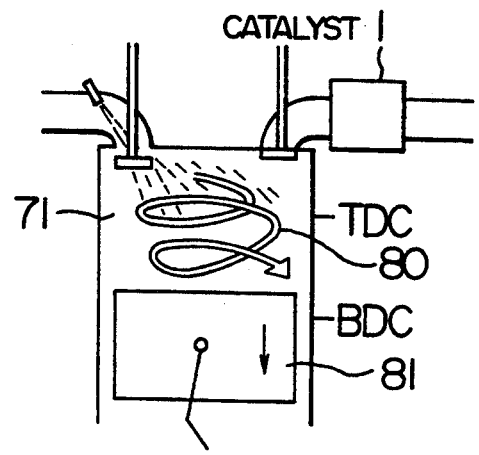
FIG. 53 is a simplified view showing flow of intake mixture.

As shown in FIG. 53, the swirling flow becomes stronger in the later period of the intake stroke, and the effect achieved by mixing fuel is more significant. Or, when the fuel is injected in the later period of the intake stroke, the fuel is not deposited on the top of piston 81 and not accumulated, therefore, the quantity of HC discharge in the later half period of the exhaust stroke does not increase. Thus, when the fuel is injected in the intake stroke, since the quantity of HC discharge is levelled, the reduction efficiency of NOx reducing catalyst 1 becomes high. Moreover, the injection valve 74 may be also an injection valve of the type for atomizing fuel by air flow.

Figure 54:
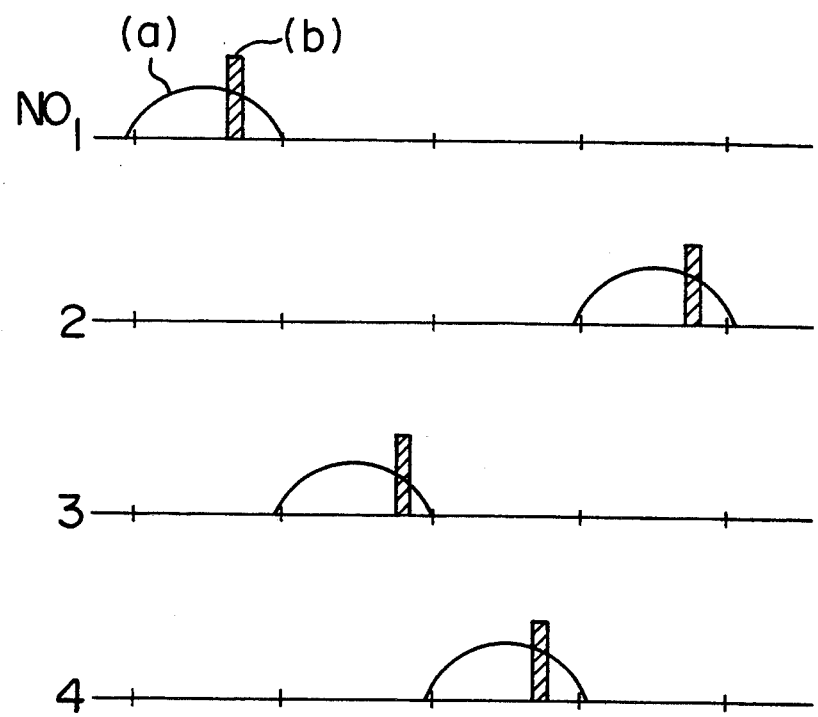
FIG. 54 is a chart showing a relationship between intake stroke and fuel injection timing.

FIG. 54 shows injection timing of fuel into each of the four cylinders. An intake stroke is indicated by (a), and fuel injection in the intake stroke is indicated by (b).

Figure 55:
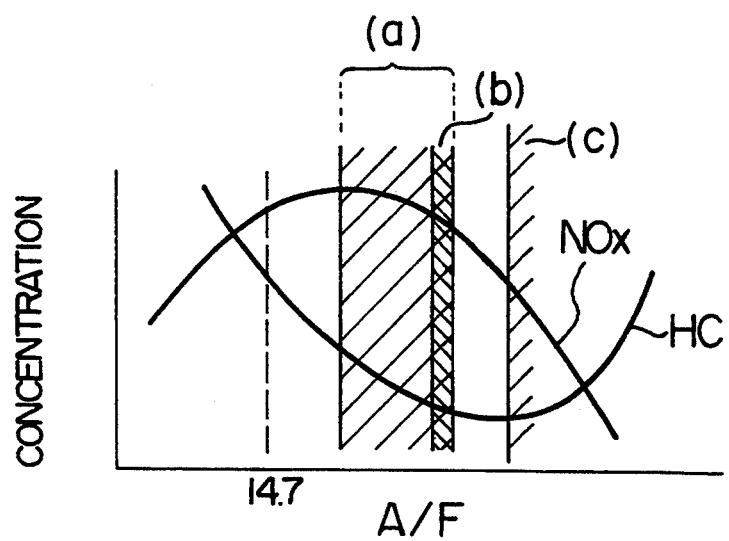
FIG. 55 is a graph showing exhaust characteristics.

A still further embodiment is shown in FIG. 55. As shown in FIG. 55, when there are a plurality of values of air-fuel ratio (a) at which NOx-HC ratio reaches an optimum value, the fuel-leanest air-fuel ratio (b) among them is set as a target control value. However, when the leanest air-fuel ratio is larger than a lean limit air-fuel ratio (c), the lean limit air-fuel ratio is set as the target air-fuel ratio.

Figure 56:
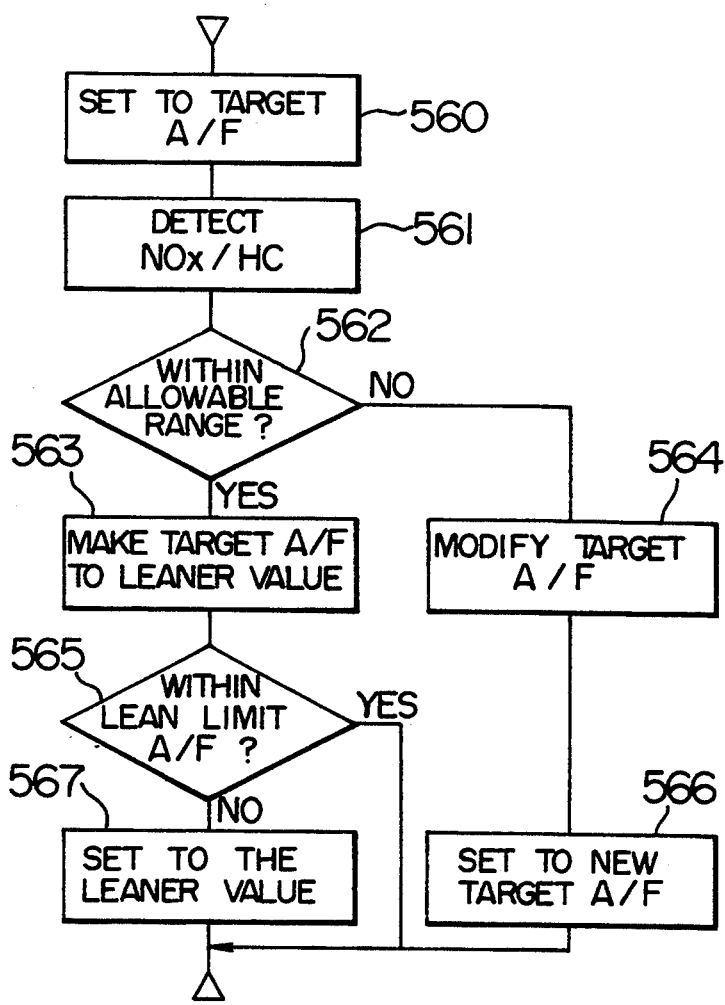
FIG. 56 is a flowchart showing a controlling process.

FIG. 56 shows a flowchart of such control. First, control is set to a target air-fuel ratio at a step 560, and the NOx-HC ratio is detected at a step 561. When this detected value is judged to be within an allowable range at a step 562, the target air-fuel ratio is made to be a leaner value at a step 563. When the leaner air-fuel ratio is judged to be smaller than the lean limit air-fuel ratio at a step 565, the target air-fuel ratio is set to be the leaner value at a step 567. When the leaner air-fuel ratio is judged to be larger than the leaner limit air-fuel ratio, the target air-fuel ratio is not set to the leaner value. When the target air-fuel ratio is judged to be out of the allowable range at a step 563, the target air-fuel ratio is modified to be within the allowable range at a step 564, and the air-fuel ratio is controlled to this new target air-fuel ratio at a step 566.

Figure 57:
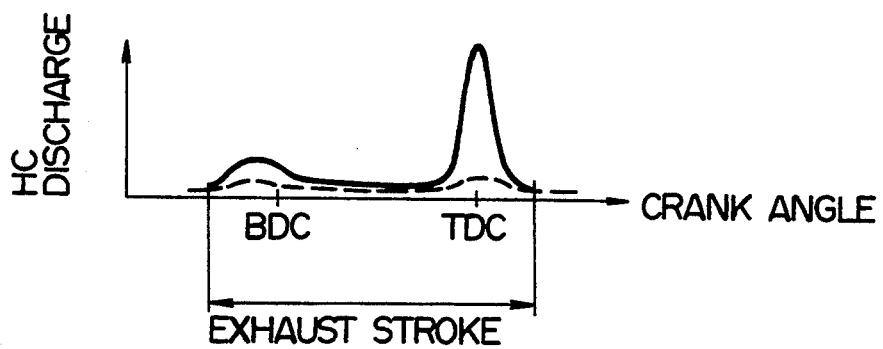
FIG. 57 is a graph showing a HC discharge characteristic.

FIG. 57 shows a still another embodiment. This embodiment includes a means for levelling the quantity of HC discharge by varying the operation timing of an intake valve. FIG. 57 shows the quantity of HC discharge in an exhaust stroke. Liquid films which are deposited on top of the piston and the cylinderhead are discharged at the beginning and the end of the exhaust stroke. It is necessary to decrease the variation of HC discharge. In the case of this embodiment, the quantity of HC discharge is levelled as shown by a dotted line.

Figure 58:
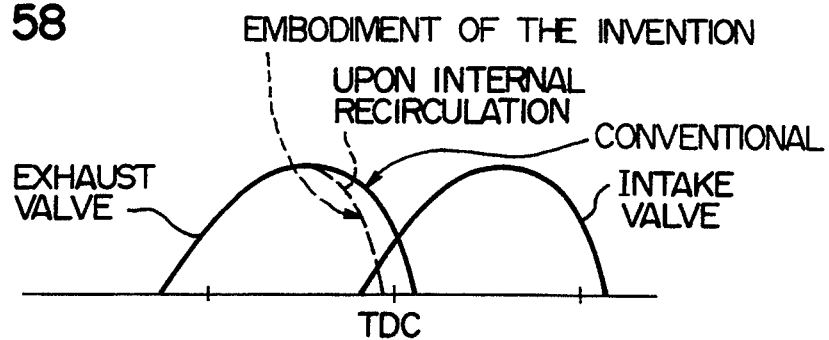
FIG. 58 is a graph showing valve timing characteristic.

FIG. 58 shows operation timings of the exhaust and intake valves, in which conventional operations are indicated by solid lines. The operations of the exhaust and intake valves are overlapped in the vicinity of TDC. According to an embodiment of the invention, when the quantity of HC discharge increases, e.g. in starting at low temperature, warming up in starting, and idling, the operation of the exhaust valve is controlled to be shifted as shown by a dotted line. By this operation, HC discharged to an exhaust tube is recirculated to an intake tube (internal recirculation). Thus, the quantity of HC which directly flows into the exhaust tube decreases, then the quantity of HC discharge is levelled.

FIG. 59 shows the distribution of HC in a cylinder during each stroke. Since an exhaust valve 91 is closed in advance before the end of an exhaust stroke, the HC as indicated by dots near the top of the piston is not discharged into the exhaust tube 2. Therefore, when the intake tube 92 is opened at the beginning of the intake stroke, the HC is returned into the intake tube 72 (internal recirculation). This HC again enters the cylinder 71 in the intake stroke and diffuses in the cylinder at the end of the intake stroke. Accordingly, HC diffuses in the cylinder 71 and again burns, and thereby the whole quantity of HC is decreased as shown by the dotted line in FIG. 57, and is levelled.

Figure 60:
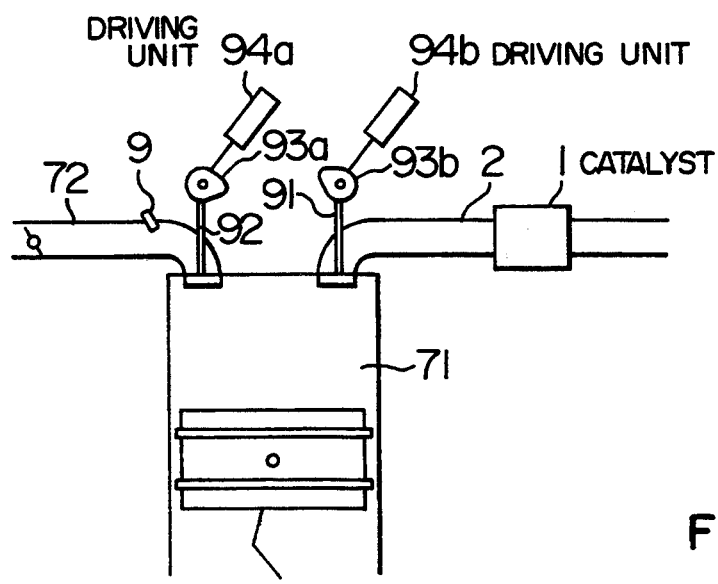
FIG. 60 is a diagrammatic illustration of still another embodiment of the invention.
Figure 61:
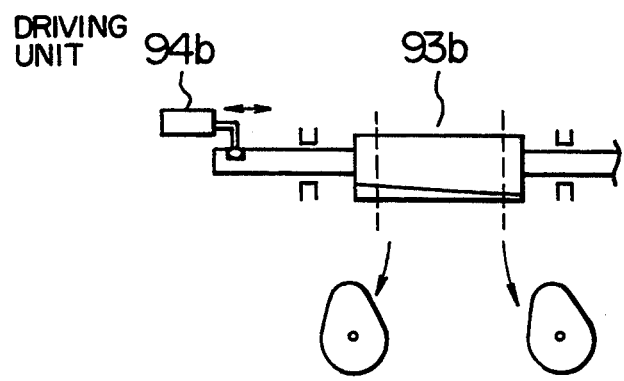
FIG. 61 is a diagrammatic illustration of a variable valve.

FIG. 60 shows an apparatus for achieving an operation described in FIGS. 57 to 59. An exhaust valve 91 and an intake valve 92 are moved upward and downward by cams 93b and 93a, respectively. The shapes of the cams are varied with driving units 94b and 94a. Since levelling of the HC discharge is achieved by an operation of an exhaust valve 91, which is controlled by the driving unit 94b, the cleaning efficiency of the NOx reducing catalyst can be improved by making the timing of the operation of the valve variable. FIG. 61 shows a method of varying the shape of the cam. The cam has shapes which differ at the sections (a) and (b). Therefore, the face of the cam varies by moving the cam 93b with the driving unit 94b rightward and leftward.

According to the present invention, NOx can be efficiently reduced in any state of running of an internal combustion engine, therefore, compliance with the regulation relating to exhaust and fuel consumption can be achieved at a higher level simultaneously.

What is claimed is:

1. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:
   controlling an air-fuel mixture, supplied to the internal combustion engine, at a level leaner than a theoretical air-fuel ratio, but not leaner than a lean combustion limit; and
   controlling the concentration of HC in the exhaust gas flowing into the NOx reducing catalyst so that a concentration ratio NOx/HC in the exhaust gas flowing into the NOx reducing catalyst falls within a range where the concentration of the HC is greater than that of the NOx.

2. A method according to claim 1, wherein said step of controlling the HC concentration includes a step of controlling the ignition timing of the internal combustion engine.

3. A method according to claim 1, wherein said step of controlling the HC concentration includes a step of supplying a controlled amount of secondary air upstream of the NOx reducing catalyst.

4. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:
   controlling an air-fuel mixture, supplied to internal combustion engine, at a level leaner than a theoretical air-fuel ratio, but not leaner than a lean combustion limit; and
   controlling the concentration of HC in the exhaust gas flowing into the NOx reducing catalyst so that a concentration ratio NOx/HC in the exhaust gas flowing into the NOx reducing catalyst falls within a predetermined range not greater than 1.0.

5. A method according to claim 4, wherein said step of controlling the HC concentration includes a step of controlling the ignition timing of the internal combustion engine.

6. A method according to claim 4, wherein said step of controlling the HC concentration includes a step of supplying a controlled amount of secondary air upstream of the NOx reducing catalyst.

7. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:
   controlling an air-fuel mixture, supplied to internal combustion engine, at a level leaner than a theoretical air-fuel ratio, but not leaner than a lean combustion limit; and
   controlling the concentration of HC in the exhaust gas flowing into the NOx reducing catalyst so that a concentration ratio NOx/HC in the exhaust gas flowing into the NOx reducing catalyst falls within a predetermined range not less than 0.7.

8. A method according to claim 7, wherein said step of controlling the HC concentration includes a step of controlling the ignition timing of the internal combustion engine.

9. A method according to claim 7, wherein said step of controlling the HC concentration includes a step of supplying a controlled amount of secondary air upstream of the NOx reducing catalyst.

10. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:
    controlling an air-fuel mixture, supplied to internal combustion engine, at a level leaner than a theoretical air-fuel ratio, but not leaner than a lean combustion limit; and
    controlling the concentration of HC in the exhaust gas flowing into the NOx reducing catalyst so that a concentration ratio NOx/HC in the exhaust gas flowing into the NOx reducing catalyst falls within a predetermined range between a first predetermined value not less than 1.0 and a second predetermined value not greater than 0.70.

11. A method according to claim 10, wherein said step of controlling the HC concentration includes a step of controlling the ignition timing of the internal combustion engine.

12. A method according to claim 10, wherein said step of controlling the HC concentration includes a step of supplying a controlled amount of secondary air upstream of the NOx reducing catalyst.

13. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:
    controlling an air-fuel mixture, supplied to internal combustion engine, at a level leaner than a theoretical air-fuel ratio, but not leaner than a lean combustion limit;
    detecting a concentration ratio NOx/HC in the exhaust gas flowing into the NOx reducing catalyst;

comparing the detected NOx/HC value with a predetermined range of values where the concentration of the HC is greater than that of the NOx; and controlling the concentration of HC in the exhaust gas flowing into the NOx reducing catalyst so that the detected NOx/HC value falls within the predetermined range in response to the comparison.

14. A method according to claim 13, wherein said step of controlling the HC concentration includes a step of controlling the ignition timing of the internal combustion engine.

15. A method according to claim 13, wherein said step of controlling the HC concentration includes a step of supplying a controlled amount of secondary air upstream of the NOx reducing catalyst.

16. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:

controlling an air-fuel mixture, supplied to internal combustion engine, at a level leaner than a theoretical air-fuel ratio, but not leaner than a lean combustion limit;

detecting a concentration ratio NOx/HC in the exhaust gas flowing into the NOx reducing catalyst;

comparing the detected NOx/HC value with a predetermined range of values where the NOx/HC value is not greater than 1.0; and controlling, in response to the comparison, the concentration of HC in the exhaust gas flowing into the NOx reducing catalyst so that the detected NOx/HC value falls within the predetermined range.

17. A method according to claim 16, wherein said step of controlling the HC concentration includes a step of controlling the ignition timing of the internal combustion engine.

18. A method according to claim 16, wherein said step of controlling the HC concentration includes a step of supplying a controlled amount of secondary air upstream of the NOx reducing catalyst.

19. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:

controlling an air-fuel mixture, supplied to internal combustion engine, at a level leaner than a theoretical air-fuel ratio, but not leaner than a lean combustion limit;

detecting a concentration ratio NOx/HC in the exhaust gas flowing into the NOx reducing catalyst;

comparing the detected NOx/HC value with a predetermined range where the NOx/HC value is not less than 0.7; and controlling, in response to the comparison, the concentration of HC in the exhaust gas flowing into the NOx reducing catalyst so that the detected NOx/HC value falls within the predetermined range.

20. A method according to claim 19, wherein said step of controlling the HC concentration includes a step of controlling the ignition timing of the internal combustion engine.

21. A method according to claim 19, wherein said step of controlling the HC concentration includes a step of supplying a controlled amount of secondary air upstream of the NOx reducing catalyst.

22. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:

controlling an air-fuel mixture, supplied to internal combustion engine, at a level leaner than a theoretical air-fuel ratio, but not leaner than a lean combustion limit;

detecting a concentration ratio NOx/HC in the exhaust gas flowing into the NOx reducing catalyst;

comparing the detected NOx/HC value with a predetermined range between a first predetermined value not less than 1.0 and a second predetermined value not greater than 0.7; and controlling, in response to the comparison, the concentration of HC in the exhaust gas flowing into the NOx reducing catalyst so that the detected NOx/HC value falls within the predetermined range.

23. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:

controlling an air-fuel mixture, supplied to internal combustion engine, at a level leaner than a theoretical air-fuel ratio, but not leaner than a lean combustion limit;

determining whether a concentration ratio NOx/HC in the exhaust gas flowing into the NOx reducing catalyst falls within a predetermined range where the concentration of HC is greater than that of NOx; and modifying a current air-fuel ratio to a leaner air-fuel ratio in a case where the NOx/HC has been determined to fall within the predetermined range.

24. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:

controlling an air-fuel mixture, supplied to internal combustion engine, at a level leaner than a theoretical air-fuel ratio, but not leaner than a lean combustion limit;

determining whether a concentration ratio NOx/HC in the exhaust gas flowing into the NOx reducing catalyst falls within a predetermined range where the concentration of HC is greater than that of NOx;

modifying a current air-fuel ratio to a leaner air-fuel ratio in a case where the NOx/HC has been determined to fall within the predetermined range; and modifying, in a case where the NOx/Hc has been determined not to fall within the predetermined range, the current air-fuel ratio to a new air-fuel ratio which causes the NOx/HC ratio to fall within the predetermined range.

25. A method of controlling the efficiency of reducing NOx in an exhaust gas issued from an internal combustion engine, by a NOx reducing catalyst disposed in an exhaust system of the internal combustion engine, through which the exhaust gas of oxidizing atmosphere passes, comprising:

controlling an air-fuel mixture, supplied to internal combustion engine, at a level leaner than a theoretical air-fuel ratio, but not leaner than a lean combustion limit; and controlling the concentration of HC in the exhaust gas flowing into the NOx reducing catalyst so that the concentration of HC is greater than the concentration of NOx in the exhaust gas.

* * * * *